US011054421B2

(12) United States Patent
Getman et al.

(10) Patent No.: US 11,054,421 B2
(45) Date of Patent: Jul. 6, 2021

(54) COMPOSITIONS, METHODS AND KITS TO DETECT HERPES SIMPLEX VIRUS NUCLEIC ACIDS

(71) Applicant: Gen-Probe Incorporated, San Diego, CA (US)

(72) Inventors: Damon Kittredge Getman, Poway, CA (US); Aparna Aiyer, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 16/600,317

(22) Filed: Oct. 11, 2019

(65) Prior Publication Data

US 2020/0033339 A1    Jan. 30, 2020

Related U.S. Application Data

(60) Continuation of application No. 16/046,429, filed on Jul. 26, 2018, now Pat. No. 10,488,412, which is a continuation of application No. 15/487,240, filed on Apr. 13, 2017, now Pat. No. 10,073,094, which is a division of application No. 14/395,039, filed as application No. PCT/US2013/037808 on Apr. 23, 2013, now Pat. No. 9,624,557.

(60) Provisional application No. 61/773,718, filed on Mar. 6, 2013, provisional application No. 61/748,854, filed on Jan. 4, 2013, provisional application No. 61/637,769, filed on Apr. 24, 2012.

(51) Int. Cl.

| | | |
|---|---|---|
| *C12Q 1/00* | (2006.01) | |
| *C12Q 1/6813* | (2018.01) | |
| *C12Q 1/70* | (2006.01) | |
| *G01N 33/569* | (2006.01) | |
| *A61K 31/7088* | (2006.01) | |
| *A61K 39/245* | (2006.01) | |
| *C07K 14/035* | (2006.01) | |
| *C07K 16/08* | (2006.01) | |
| *C12N 15/09* | (2006.01) | |
| *G01N 33/53* | (2006.01) | |
| *A61K 38/00* | (2006.01) | |
| *A61K 39/00* | (2006.01) | |
| *A61K 45/00* | (2006.01) | |
| *A61K 48/00* | (2006.01) | |
| *C07K 19/00* | (2006.01) | |

(52) U.S. Cl.
CPC ....... *G01N 33/569* (2013.01); *A61K 31/7088* (2013.01); *A61K 39/245* (2013.01); *C07K 14/035* (2013.01); *C07K 16/08* (2013.01); *C12N 15/09* (2013.01); *C12Q 1/705* (2013.01); *G01N 33/53* (2013.01); *A61K 38/00* (2013.01); *A61K 39/00* (2013.01); *A61K 45/00* (2013.01); *A61K 48/00* (2013.01); *C07K 19/00* (2013.01)

(58) Field of Classification Search
None
See application file for complete search history.

(56) References Cited

U.S. PATENT DOCUMENTS

| | | |
|---|---|---|
| 9,624,557 B2 | 4/2017 | Getman et al. |
| 10,073,094 B2 | 9/2018 | Getman et al. |
| 10,488,412 B2 | 11/2019 | Getman et al. |
| 2011/0091885 A1 | 4/2011 | Schmitt et al. |

FOREIGN PATENT DOCUMENTS

| | | |
|---|---|---|
| CN | 102337355 A | 2/2012 |
| EP | 2098599 A1 | 9/2009 |
| WO | WO 2005/116250 A2 | 10/2005 |

OTHER PUBLICATIONS

Kessler et al. Detection of Herpes Simplex Virus DNA by Real-Time PCR. J. Clin. Microbiol., 2000, 38: 2638-2642.*
Srivastava GP, Xu D. Genome-scale probe and primer design with PRIMEGENS. Methods Mol Biol. 2007;402:159-176.*
APO Notice of Acceptance, Australian Patent Application No. 2013205110, dated Sep. 29, 2016.
APO Patent Examination Report No. 1, Australian Patent Application No. 2013205110, dated Dec. 23, 2014.
Burrel et al., "Genotypic characterization of herpes simplex virus DNA polymerase UL42 processivity factor," Antiviral Research, 2012, 93:199-203, Elsevier B.V.
EPO Communication Pursuant to Article 94(3), European Patent Application No. 13720689.2, dated Jun. 23, 2016.
EPO Communication Pursuant to Article 94(3), European Patent Application No. 13720689.2, dated Feb. 27, 2017.
File history of U.S. Appl. No. 15/487,240, filed Apr. 13, 2017, published as 2017-0285025 on Oct. 5, 2017, issued as U.S. Pat. No. 10,073,094 on Sep. 11, 2018
GenBank: GU071091.1. Enterobacteria phage T7, complete genome. Dated Nov. 15, 2009.
Marshall. Graphical Design of Primers with PerlPrimer. Methods Mal Biol. 402:403-14 (2007).
Melani et al. Detection of herpes simplex virus type 1 DNA in bilateral human trigeminal ganglia and optic nerves by polymerase chain reaction. J Med Virol. Dec. 2006;78(12):1584-7.
PCT International Preliminary Report on Patentability, Application No. PCT/US2013/037808, dated Oct. 28, 2014.
PCT Search Report, International Application No. PCT/US2013/037808, dated Aug. 26, 2013.

(Continued)

*Primary Examiner* — Nianxiang Zou
(74) *Attorney, Agent, or Firm* — McNeill Baur PLLC

(57) ABSTRACT

The disclosed invention is related to methods, compositions, kits and isolated nucleic acid sequences for targeting Herpes Simplex Virus (HSV) nucleic acid (e.g., HSV-1 and/or HSV-2 nucleic acid). Compositions include amplification oligomers, detection probe oligomers and/or target capture oligomers. Kits and methods comprise at least one of these oligomers.

20 Claims, 5 Drawing Sheets
Specification includes a Sequence Listing.

(56) References Cited

OTHER PUBLICATIONS

PCT Written Opinion, International Application No. PCT/US2013/037808, dated Aug. 26, 2013.

Peeters et al. Real-Time PCR to Study the Sequence Specific Magnetic Purification of DNA. Biotechnol Prag. Nov.-Dec. 2010;26(6):1678-84. Epub Sep. 27, 2010.

Rose et al. Evaluation of real-time polymerase chain reaction assays for the detection of herpes simplex virus in swab specimens. Eur J Clin Microbial Infect Dis. Sep. 2008;27(9):857-61. Epub Mar. 6, 2008.

USPTO Notice of Allowance, U.S. Appl. No. 15/487,240, dated May 22, 2018.

USPTO Notice of Allowance, U.S. Appl. No. 14/395,039, dated Dec. 2, 2016.

USPTO Office Action, U.S. Appl. No. 15/487,240, dated Dec. 4, 2017.

USPTO Office Action, U.S. Appl. No. 14/395,039, dated Jul. 21, 2016.

Vue et al. Development of a sensitive and quantitative assay for spring viremia of carp virus based on real-time RT-DCR. J Virol Methods. Sep. 2008;152(1-2):43-8. Epub Jul. 21, 2008.

Whiley et al. Detection and differentiation of herpes simplex virus types 1 and 2 by a duplex LightCycler PCR that incorporates an internal control PCR reaction. J Clin Viral. May 2004;30(1):32-8.

Yue et al. Development of a sensitive and quantitative assay for spring viremia of carp virus based on real-time RT-PCR. J Viral Methods. Sep. 2008;152(1-2):43-8. Epub Jul. 21, 2008.

\* cited by examiner

```
         ....|....| ....|....| ....|....| ....|....| ....|....| ....|....|
              5         15         25         35         45         55
         gcgcggcggg cctgccgtag tttctggctc ggtgagcgac ggtccggttg cttgggtccc ....|....| ....|....| ....|....| ....|....| ....|....| ....|....|
             65         75         85         95        105        115
         ctggctgcca tcaaaacccc accctcgcag cggcatacgc ccccteegeg teccgcaccc ....|....| ....|....| ....|....| ....|....| ....|....| ....|....|
            125        135        145        155        165        175
         gagacceegg ceeggetgee ctcaccaccg aagcccacct cgtcactgtg gggtgttccc ....|....| ....|....| ....|....| ....|....| ....|....| ....|....|
            185        195        205        215        225        235
         agcccgcgtt gggatgacgg attccctgg cggtgtggcc cccgcctccc acgtggagga ....|....| ....|....| ....|....| ....|....| ....|....| ....|....|
            245        255        265        275        285        295
         cgcgtcggac gcgtccctcg ggcagccgga ggaggggcg ccctgccagg tggtcctgca ....|....| ....|....| ....|....| ....|....| ....|....| ....|....|
            305        315        325        335        345        355
         gggcgccgag cttaatggaa tcctacaggc gtttgccccg ctgcgcacga gccttctgga ....|....| ....|....| ....|....| ....|....| ....|....| ....|....|
            365        375        385        395        405        415
         ctcgcttctg gttatgggag accggggcat ccttatccat aacacgatct ttggggagca ....|....| ....|....| ....|....| ....|....| ....|....| ....|....|
            425        435        445        455        465        475
         ggtgttcctg cccctggaac actcgcaatt cagtcggtat cgctggcgcg gacccacggc ....|....| ....|....| ....|....| ....|....| ....|....| ....|....|
            485        495        505        515        525        535
         ggcgttcctg tctctcgtgg accagaagcg ctccctcctg agcgtgtttc gcgccaacca ....|....| ....|....| ....|....| ....|....| ....|....| ....|....|
            545        555        565        575        585        595
         gtacccggac ctacgtcggg tggagttggc gatcacgggc caggcccgt ttcgcacgct ....|....| ....|....| ....|....| ....|....| ....|....| ....|....|
            605        615        625        635        645        655
         ggttcagcgc atatggacga cgacgtccga cggcgaggcc gttgagctag ccagcgagac ....|....| ....|....| ....|....| ....|....| ....|....| ....|....|
            665        675        685        695        705        715
         gctgatgaag cgcgaactga cgagctttgt ggtgctggtt ccccagggaa ccccgacgt
```

FIG. 1A

```
         ....|....| ....|....| ....|....| ....|....| ....|....| ....|....|
             725        735        745        755        765        775
         tcagttgcgc ctgacgaggc cgcagctcac caaggtcctt aacgcgaccg gggccgatag ....|....| ....|....| ....|....| ....|....| ....|....| ....|....|
             785        795        805        815        825        835
         tgccacgccc accacgttcg agctcgggt taacggcaaa ttttccgtgt tcaccacgag ....|....| ....|....| ....|....| ....|....| ....|....| ....|....|
             845        855        865        875        885        895
         tacctgcgtc acatttgctg cccgcgagga gggcgtgtcg tccagcacca gcacccaggt ....|....| ....|....| ....|....| ....|....| ....|....| ....|....|
             905        915        925        935        945        955
         ccagatcctg tccaacgcgc tcaccaaggc gggccaggcg gccgccaacg ccaagacggt ....|....| ....|....| ....|....| ....|....| ....|....| ....|....|
             965        975        985        995       1005       1015
         gtacggggaa aatacccatc gtaccttctc tgtggtcgtc gacgattgca gcatgcgggc ....|....| ....|....| ....|....| ....|....| ....|....| ....|....|
            1025       1035       1045       1055       1065       1075
         ggtgctccgg cgactgcagg tcgccggggg caccctcaag ttcttcctca cgaccccgt ....|....| ....|....| ....|....| ....|....| ....|....| ....|....|
            1085       1095       1105       1115       1125       1135
         ccccagtctg tgcgtcaccg ccaccggtcc caacgcggta tcggcggtat ttctcctgaa ....|....| ....|....| ....|....| ....|....| ....|....| ....|....|
            1145       1155       1165       1175       1185       1195
         accccagaag atttgcctgg actggctggg tcatagccag gggtctcctt ccgccgggag ....|....| ....|....| ....|....| ....|....| ....|....| ....|....|
            1205       1215       1225       1235       1245       1255
         ctcggcctcc cgggcctctg ggagcgagcc aacagacagc caggactccg cgtcggacgc ....|....| ....|....| ....|....| ....|....| ....|....| ....|....|
            1265       1275       1285       1295       1305       1315
         ggtcagccac ggcgatccgg aagacctcga tggcgctgcc cgggcgggag aggcggggc ....|....| ....|....| ....|....| ....|....| ....|....| ....|....|
            1325       1335       1345       1355       1365       1375
         ctcgtacgcc tgtccgatgc cgtcgtcgac cacgcgggtc actcccacga ccaagcgggg ....|....| ....|....| ....|....| ....|....| ....|....| ....|....|
            1385       1395       1405       1415       1425       1435
         gcgctcgggg ggcgaggatg cgcacgcgga cacggcccta agaaaccta agacggggtc
```

FIG. 1B

```
    ....|....| ....|....| ....|....| ....|....| ....|....| ....|....|
      1445       1455       1465       1475       1485       1495
    gcccaccgca ccccngcccg cagatccagt cccnctggac acggaggacg actccgatgc ....|....| ....|....| ....|....| ....|....| ....|....| ....|....|
      1505       1515       1525       1535       1545       1555
    ggcggacggg acggcggccc gtcccgccgc tccagacgcc cgaagcggaa gccgttacgc ....|....| ....|....| ....|....| ....|....| ....|....| ....|....|
      1565       1575       1585       1595       1605       1615
    gtgttacttt cgcgacctcc cgaccggaga agcaagcccc ggcgccttct ccgccttccg ....|....| ....|....| ....|....| ....|....| ....|....| ....|....|
      1625       1635       1645       1655       1665       1675
    gggggccccc caaacccgt ctggttttgg attccctga cggggcgggg ccttagcggc ....|....| ....|....| ....|....| ....|....|
      1685       1695       1705       1715
    cgcccaaccc tcgcaacatc ccggggttaa tgtaaataaa
```

FIG. 1C

```
          ....|....| ....|....| ....|....| ....|....| ....|....| ....|....|
               5          15         25         35         45         55
          atggctcatc ttcccggcgg tgcggccgcc gcccccpttt cggaggacgc gatcccgtcg ....|....| ....|....| ....|....| ....|....| ....|....| ....|....|
              65         75         85         95        105        115
          ccgcgcgagc ggacggaaga ctggccgccc tgccagatag tgctgcaggg cgccgagctg ....|....| ....|....| ....|....| ....|....| ....|....| ....|....|
             125        135        145        155        165        175
          aacgggatcc tgcaggcctt tgcgccgctt cgcacgagcc ttttggactc gctcctggtc ....|....| ....|....| ....|....| ....|....| ....|....| ....|....|
             185        195        205        215        225        235
          gtgggcgacc gaggcatcct tgtacataac gcgatttcg gcgagcaggt gtttctgccc ....|....| ....|....| ....|....| ....|....| ....|....| ....|....|
             245        255        265        275        285        295
          ctcgaccatt cgcagttcag tcgctatcga tggggcggac ccaccgcggc gttcctgtct ....|....| ....|....| ....|....| ....|....| ....|....| ....|....|
             305        315        325        335        345        355
          ctcgtggacc agaagcgatc cctgctgagc gtgtttcgcg ccaaccagta ccctgacctg ....|....| ....|....| ....|....| ....|....| ....|....| ....|....|
             365        375        385        395        405        415
          cggcgggtgg agctgacggt cacgggccag gccccgtttc gcacgctggt gcagcgcata ....|....| ....|....| ....|....| ....|....| ....|....| ....|....|
             425        435        445        455        465        475
          tggacgaccg cgtccgacgg agaggccgtg gagcttgcca gcgagacgct catgaaacgc ....|....| ....|....| ....|....| ....|....| ....|....| ....|....|
             485        495        505        515        525        535
          gagttgacga gcttcgcggt actactcccc cagggcgacc ccgacgtcca gctgcgcctc ....|....| ....|....| ....|....| ....|....| ....|....| ....|....|
             545        555        565        575        585        595
          acgaagcccc agctcacgaa ggtggtgaac gccgtcgggg acgagaccgc caaacccacc ....|....| ....|....| ....|....| ....|....| ....|....| ....|....|
             605        615        625        635        645        655
          acgttcgagc tcggccccaa cggcaagttt tccgtgttta acgcgcgcac ctgcgtcacc ....|....| ....|....| ....|....| ....|....| ....|....| ....|....|
             665        675        685        695        705        715
          tttgccgccc gcgaggaggg cgcgtcgtcc agcaccagcg cccaggtcca gattctgacc
```

FIG. 2A

```
        ....|....| ....|....| ....|....| ....|....| ....|....| ....|....|
           725        735        745        755        765        775
        agcgcgctga agaaggcggg ccaagcggcc gccaacgcca agacggtcta cggggaaaac ....|....| ....|....| ....|....| ....|....| ....|....| ....|....|
           785        795        805        815        825        835
        acacaccgca cattctcggt ggtcgtcgac gactgcagca tgcgggcggt cctccggcgg ....|....| ....|....| ....|....| ....|....| ....|....| ....|....|
           845        855        865        875        885        895
        ctccaggtcg gcggggggac cctcaagttc ttcctcacgg ccgacgtccc cagcgtgtgt ....|....| ....|....| ....|....| ....|....| ....|....| ....|....|
           905        915        925        935        945        955
        gtcaccgcca ccggccccaa cgcggtgtcg gcggtgtttc ttttaaaacc ccagcgggtc ....|....| ....|....| ....|....| ....|....| ....|....| ....|....|
           965        975        985        995       1005       1015
        tgcctgaact ggctcggccg gagcccgggt tcctcgaccg ggagcttggc gtcccaggac ....|....| ....|....| ....|....| ....|....| ....|....| ....|....|
          1025       1035       1045       1055       1065       1075
        tctcgggccg gcccgaccga cagccaggac tcctcctccg agccggacgc gggcgaccgc ....|....| ....|....| ....|....| ....|....| ....|....| ....|....|
          1085       1095       1105       1115       1125       1135
        ggcgccccag aagaagaagg cctcgagggc caggcccggg taccgcccgc gttcccggaa ....|....| ....|....| ....|....| ....|....| ....|....| ....|....|
          1145       1155       1165       1175       1185       1195
        ccgccgggaa ccaagcggag gcaccccggg gccgaagttg tccccgcgga cgacgccacc ....|....| ....|....| ....|....| ....|....| ....|....| ....|....|
          1205       1215       1225       1235       1245       1255
        aagcgcccga agacgggcgt gcccgccgcc ccacgcgag ccgagtcgcc cccctctcc ....|....| ....|....| ....|....| ....|....| ....|....| ....|....|
          1265       1275       1285       1295       1305       1315
        gcgagatacg gacccgaggc ggcggagggt ggtggggacg gcggccgcta cgcgtgctac ....|....| ....|....| ....|....| ....|....| ....|....| ....|....|
          1325       1335       1345       1355       1365       1375
        tttcgcgacc tccagaccgg cgacgcgagc cccagccccc tctccgcctt ccggggtccc ....|....| ....|....| ....|....| ...
          1385       1395       1405
        caaagacccc catacggctt tgggttgccc tga
```

FIG. 2B

SEQUENCE LISTING

<160> NUMBER OF SEQ ID NOS: 76

<210> SEQ ID NO 1
<211> LENGTH: 1720
<212> TYPE: DNA
<213> ORGANISM: Herpes simplex virus type 1
<300> PUBLICATION INFORMATION:
<308> DATABASE ACCESSION NUMBER: GenBank Accession No. GU734771.1
      (GI:290766003)
<309> DATABASE ENTRY DATE: 2004-04-27
<313> RELEVANT RESIDUES IN SEQ ID NO: (92815)..(94534)

<400> SEQUENCE: 1

```
gcgcggcggg cctgccgtag tttctggctc ggtgagcgac ggtccggttg cttgggtccc    60
ctggctgcca tcaaaacccc accctcgcag cggcatacgc ccctccgcg tcccgcaccc    120 gagaccccgg cccggctgcc ctcaccaccg aagcccacct cgtcactgtg gggtgttccc    180
agcccgcgtt gggatgacgg attcccctgg cggtgtggcc cccgcctccc acgtggagga    240
cgcgtcggac gcgtcccctcg ggcagccgga ggaggggggcg ccctgccagg tggtcctgca   300
gggcgccgag cttaatggaa tcctacaggc gtttgccccg ctgcgcacga gccttctgga    360
ctcgcttctg gttatgggag accggggcat cctatccat aacacgatct ttggggagca    420
ggtgttcctg cccctggaac actcgcaatt cagtcggtat cgctggcgcg gacccacggc   480
ggcgttcctg tctctcgtgg accagaagcg ctccctcctg agcgtgtttc gcgccaacca   540
gtacccggac ctacgtcggg tggagttggc gatcacgggc caggccccgt tcgcacgct    600
```

```
ggttcagcgc atatggacga cgacgtccga cggcgaggcc gttgagctag ccagcgagac    660
gctgatgaag cgcgaactga cgagctttgt ggtgctggtt ccccagggaa ccccgacgt     720 tcagttgcgc ctgacgaggc cgcagctcac caaggtcctt aacgcgaccg gggccgatag    780
tgccacgccc accacgttcg agctcggggt taacggcaaa ttttccgtgt tcaccacgag    840
tacctgcgtc acatttgctg cccgcgagga gggcgtgtcg tccagcacca gcacccaggt    900
ccagatcctg tccaacgcgc tcaccaaggc gggccaggcg ccgccaacg ccaagacggt     960 gtacggggaa atacccatc gtaccttctc tgtggtcgtc gacgattgca gcatgcgggc    1020
ggtgctccgg cgactgcagg tcgccggggg caccctcaag ttcttcctca cgaccccgt    1080 ccccagtctg tgcgtcaccg ccaccggtcc caacgcggta tcggcggtat ttctcctgaa   1140
accccagaag atttgcctgg actggctggg tcatagccag gggtctcctt ccgccgggag   1200
ctcggcctcc cgggcctctg ggagcgagcc aacagacagc caggactccg cgtcggacgc   1260
ggtcagccac ggcgatccgg aagacctcga tggcgctgcc cgggcgggag aggcgggggc   1320
ctcgtacgcc tgtccgatgc cgtcgtcgac cacgcgggtc actcccacga ccaagcgggg   1380
gcgctcgggg ggcgaggatg cgcacgcgga cacggcccta agaaaccta agacggggtc    1440 gcccaccgca cccccgcccg cagatccagt ccccctggac acggaggacg actccgatgc   1500 ggcgacggg acgcggccc gtcccgccgc tccagacgcc cgaagcggaa gccgttacgc    1560
gtgttacttt cgcgacctcc cgaccggaga agcaagcccc ggcgccttct ccgccttccg   1620
ggggggcccc caaacccgt ctggttttgg attcccctga cggggcgggg ccttagcggc    1680
cgcccaaccc tcgcaacatc ccggggttaa tgtaaataaa                          1720

<210> SEQ ID NO 2
<211> LENGTH: 1413
<212> TYPE: DNA
<213> ORGANISM: Herpes simplex virus type 2 (strain HG52)
<300> PUBLICATION INFORMATION:
<308> DATABASE ACCESSION NUMBER: GenBank Accession No. Z86099.2
      (GI:6572414)
<309> DATABASE ENTRY DATE: 2006-11-14
<313> RELEVANT RESIDUES IN SEQ ID NO: (93769)..(95181)

<400> SEQUENCE: 2
atggctcatc ttcccggcgg tgcggccgcc gcccccttt cggaggacgc gatcccgtcg      60
ccgcgcgagc ggacggaaga ctggccgccc tgccagatag tgctgcaggg cgccgagctg     120
aacgggatcc tgcaggcctt tgcgccgctt cgcacgagcc ttttggactc gctcctggtc     180
gtgggcgacc gaggcatcct tgtacataac gcgattttcg gcgagcaggt gtttctgccc     240
ctcgaccatt cgcagttcag tcgctatcga tggggcggac ccaccgcggc gttcctgtct     300
ctcgtggacc agaagcgatc cctgctgagc gtgtttcgcg ccaaccagta ccctgacctg     360
cggcgggtgg agctgacggt cacgggccag gccccgtttc gcacgctggt gcagcgcata     420
tggacgaccg cgtccgacgg agaggccgtg agcttgcca gcgagacgct catgaaacgc      480
gagttgacga gcttcgcggt actactcccc cagggcgacc ccgacgtcca gctgcgcctc     540
acgaagcccc agctcacgaa ggtggtgaac gccgtcgggg acgagaccgc caaacccacc     600
acgttcgagc tcggccccaa cggcaagttt tccgtgttta acgcgcgcac ctgcgtcacc     660
tttgccgccc gcgaggaggg cgcgtcgtcg agcaccagcg cccaggtcca gattctgacc     720
agcgcgctga gaaggcggg ccaagcgcc gccaacgcca agacggtcta cggggaaaac       780
acacaccgca cattctcggt ggtcgtcgac gactgcagca tgcgggcggt cctccggcgg    840
```

-continued

```
ctccaggtcg cggggggac cctcaagttc ttcctcacgg ccgacgtccc cagcgtgtgt      900
gtcaccgcca ccggcccaa cgcggtgtcg gcggtgtttc ttttaaaacc ccagcgggtc      960
tgcctgaact ggctcggccg gagcccgggt tcctcgaccg ggagcttggc gtcccaggac     1020
tctcgggccg gcccgaccga cagccaggac tcctcctccg agccggacgc gggcgaccgc     1080
ggcgccccag aagaagaagg cctcgagggc caggcccggg taccgcccgc gttcccggaa     1140
ccgccgggaa ccaagcggag gcaccccggg gccgaagttg tccccgcgga cgacgccacc     1200
aagcgcccga agacgggcgt gccgccgcc ccacgcgag ccgagtcgcc ccccctctcc      1260
gcgagatacg gacccgaggc ggcggagggt ggtggggacg gcggccgcta cgcgtgctac     1320
tttcgcgacc tccagaccgg cgacgcgagc ccagccccc tctccgcctt ccggggtccc     1380
caaagacccc catacggctt tgggttgccc tga                                 1413
```

<210> SEQ ID NO 3
<211> LENGTH: 53
<212> TYPE: DNA
<213> ORGANISM: Artificial Sequence
<220> FEATURE:
<223> OTHER INFORMATION: Synthetic Oligo

<400> SEQUENCE: 3

```
gtactggttg gcgcgaaaca tttaaaaaaa aaaaaaaaa aaaaaaaaaa aaa             53
```

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 4

```
gtactggttg gcgcgaaaca                                                 20
```

<210> SEQ ID NO 5
<211> LENGTH: 50
<212> TYPE: DNA
<213> ORGANISM: Artificial Sequence
<220> FEATURE:
<223> OTHER INFORMATION: Synthetic Oligo
<220> FEATURE:
<221> NAME/KEY: promoter
<222> LOCATION: (1)..(27)

<400> SEQUENCE: 5

```
aatttaatac gactcactat agggagattc cctggggaac cagcaccaca               50
```

<210> SEQ ID NO 6
<211> LENGTH: 23
<212> TYPE: DNA
<213> ORGANISM: Artificial Sequence
<220> FEATURE:
<223> OTHER INFORMATION: Synthetic Oligo

<400> SEQUENCE: 6

```
ttccctgggg aaccagcacc aca                                             23
```

<210> SEQ ID NO 7
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 7
gttcagcgca tatggacgac ga                                           22

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 8
agacgctgat gaagcgcgaa                                              20

<210> SEQ ID NO 9
<211> LENGTH: 18
<212> TYPE: DNA
<213> ORGANISM: Artificial Sequence
<220> FEATURE:
<223> OTHER INFORMATION: Synthetic Oligo

<400> SEQUENCE: 9
acgacgacgt ccgacggc                                                18

<210> SEQ ID NO 10
<211> LENGTH: 17
<212> TYPE: DNA
<213> ORGANISM: Artificial Sequence
<220> FEATURE:
<223> OTHER INFORMATION: Synthetic Oligo

<400> SEQUENCE: 10
ggccgttgag ctagcca                                                 17

<210> SEQ ID NO 11
<211> LENGTH: 50
<212> TYPE: DNA
<213> ORGANISM: Artificial Sequence
<220> FEATURE:
<223> OTHER INFORMATION: Synthetic Oligo
<220> FEATURE:
<221> NAME/KEY: promoter
<222> LOCATION: (1)..(27)

<400> SEQUENCE: 11
aatttaatac gactcactat agggagaggt tccctgggga accagcacca              50

<210> SEQ ID NO 12
<211> LENGTH: 23
<212> TYPE: DNA
<213> ORGANISM: Artificial Sequence
<220> FEATURE:
<223> OTHER INFORMATION: Synthetic Oligo

<400> SEQUENCE: 12
ggttccctgg ggaaccagca cca                                          23

<210> SEQ ID NO 13
<211> LENGTH: 48
<212> TYPE: DNA
<213> ORGANISM: Artificial Sequence
<220> FEATURE:
<223> OTHER INFORMATION: Synthetic Oligo
<220> FEATURE:
<221> NAME/KEY: promoter
<222> LOCATION: (1)..(27)

<400> SEQUENCE: 13
aatttaatac gactcactat agggagaaac gtggtgggtt tggcggtc        48

<210> SEQ ID NO 14
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 14
aacgtggtgg gtttggcggt c        21

<210> SEQ ID NO 15
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 15
acgtccagct gcgcctcacg a        21

<210> SEQ ID NO 16
<211> LENGTH: 19
<212> TYPE: DNA
<213> ORGANISM: Artificial Sequence
<220> FEATURE:
<223> OTHER INFORMATION: Synthetic Oligo

<400> SEQUENCE: 16
tcacgaaggt ggtgaacgc        19

<210> SEQ ID NO 17
<211> LENGTH: 53
<212> TYPE: DNA
<213> ORGANISM: Artificial Sequence
<220> FEATURE:
<223> OTHER INFORMATION: Synthetic Oligo

<400> SEQUENCE: 17
guacugguug gcgcgaaaca tttaaaaaaa aaaaaaaaa aaaaaaaaaa aaa        53

<210> SEQ ID NO 18
<211> LENGTH: 20
<212> TYPE: RNA
<213> ORGANISM: Artificial Sequence
<220> FEATURE:
<223> OTHER INFORMATION: Synthetic Oligo

<400> SEQUENCE: 18
guacugguug gcgcgaaaca        20

<210> SEQ ID NO 19
<211> LENGTH: 49
<212> TYPE: DNA
<213> ORGANISM: Artificial Sequence
<220> FEATURE:
<223> OTHER INFORMATION: Synthetic Oligo
<220> FEATURE:
<221> NAME/KEY: promoter
<222> LOCATION: (1)..(27)

<400> SEQUENCE: 19
aatttaatac gactcactat agggagatcc ctggggaacc agcaccaca        49

```
<210> SEQ ID NO 20
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 20
tccctgggga accagcacca ca                                              22

<210> SEQ ID NO 21
<211> LENGTH: 25
<212> TYPE: RNA
<213> ORGANISM: Artificial Sequence
<220> FEATURE:
<223> OTHER INFORMATION: Synthetic Oligo

<400> SEQUENCE: 21
ugaugaagcg cgaacugacu cauca                                           25

<210> SEQ ID NO 22
<211> LENGTH: 18
<212> TYPE: RNA
<213> ORGANISM: Artificial Sequence
<220> FEATURE:
<223> OTHER INFORMATION: Synthetic Oligo

<400> SEQUENCE: 22
gaugaagcgc gaacugac                                                   18

<210> SEQ ID NO 23
<211> LENGTH: 46
<212> TYPE: DNA
<213> ORGANISM: Artificial Sequence
<220> FEATURE:
<223> OTHER INFORMATION: Synthetic Oligo
<220> FEATURE:
<221> NAME/KEY: promoter
<222> LOCATION: (1)..(27)

<400> SEQUENCE: 23
aatttaatac gactcactat agggagagca ggtgcgcgcg ttaaac                    46

<210> SEQ ID NO 24
<211> LENGTH: 19
<212> TYPE: DNA
<213> ORGANISM: Artificial Sequence
<220> FEATURE:
<223> OTHER INFORMATION: Synthetic Oligo

<400> SEQUENCE: 24
gcaggtgcgc gcgttaaac                                                  19

<210> SEQ ID NO 25
<211> LENGTH: 18
<212> TYPE: DNA
<213> ORGANISM: Artificial Sequence
<220> FEATURE:
<223> OTHER INFORMATION: Synthetic Oligo

<400> SEQUENCE: 25
acgagaccgc caaaccca                                                   18

<210> SEQ ID NO 26
<211> LENGTH: 25
<212> TYPE: RNA
```

```
<213> ORGANISM: Artificial Sequence
<220> FEATURE:
<223> OTHER INFORMATION: Synthetic Oligo

<400> SEQUENCE: 26
cucggcccca acggcaaguu ccgag                                      25

<210> SEQ ID NO 27
<211> LENGTH: 20
<212> TYPE: RNA
<213> ORGANISM: Artificial Sequence
<220> FEATURE:
<223> OTHER INFORMATION: Synthetic Oligo

<400> SEQUENCE: 27
cucggcccca acggcaaguu                                            20

<210> SEQ ID NO 28
<211> LENGTH: 20
<212> TYPE: DNA
<213> ORGANISM: Artificial Sequence
<220> FEATURE:
<223> OTHER INFORMATION: Amp oligomer core sequence

<400> SEQUENCE: 28
tccctgggga accagcacca                                            20

<210> SEQ ID NO 29
<211> LENGTH: 25
<212> TYPE: DNA
<213> ORGANISM: Artificial Sequence
<220> FEATURE:
<223> OTHER INFORMATION: Amp oligomer region

<400> SEQUENCE: 29
ggttccctgg ggaaccagca ccaca                                      25

<210> SEQ ID NO 30
<211> LENGTH: 12
<212> TYPE: DNA
<213> ORGANISM: Artificial Sequence
<220> FEATURE:
<223> OTHER INFORMATION: Amp oligomer core sequence

<400> SEQUENCE: 30
tggggaacca gc                                                    12

<210> SEQ ID NO 31
<211> LENGTH: 29
<212> TYPE: DNA
<213> ORGANISM: Artificial Sequence
<220> FEATURE:
<223> OTHER INFORMATION: Amp oligomer region

<400> SEQUENCE: 31
ggttccctgg ggaaccagca ccacaaagc                                  29

<210> SEQ ID NO 32
<211> LENGTH: 7
<212> TYPE: DNA
<213> ORGANISM: Artificial Sequence
<220> FEATURE:
<223> OTHER INFORMATION: Amp oligomer core sequence

<400> SEQUENCE: 32 acgacga                                                          7
```

<210> SEQ ID NO 33
<211> LENGTH: 33
<212> TYPE: DNA
<213> ORGANISM: Artificial Sequence
<220> FEATURE:
<223> OTHER INFORMATION: Amp oligomer region

<400> SEQUENCE: 33
gttcagcgca tatggacgac gacgtccgac ggc                33

<210> SEQ ID NO 34
<211> LENGTH: 13
<212> TYPE: DNA
<213> ORGANISM: Artificial Sequence
<220> FEATURE:
<223> OTHER INFORMATION: Probe oligomer core sequence

<400> SEQUENCE: 34
gatgaagcgc gaa                13

<210> SEQ ID NO 35
<211> LENGTH: 13
<212> TYPE: RNA
<213> ORGANISM: Artificial Sequence
<220> FEATURE:
<223> OTHER INFORMATION: Probe oligomer core sequence

<400> SEQUENCE: 35
gaugaagcgc gaa                13

<210> SEQ ID NO 36
<211> LENGTH: 25
<212> TYPE: DNA
<213> ORGANISM: Artificial Sequence
<220> FEATURE:
<223> OTHER INFORMATION: Probe oligomer region

<400> SEQUENCE: 36
agacgctgat gaagcgcgaa ctgac                25

<210> SEQ ID NO 37
<211> LENGTH: 25
<212> TYPE: RNA
<213> ORGANISM: Artificial Sequence
<220> FEATURE:
<223> OTHER INFORMATION: Probe oligomer region

<400> SEQUENCE: 37
agacgcugau gaagcgcgaa cugac                25

<210> SEQ ID NO 38
<211> LENGTH: 10
<212> TYPE: DNA
<213> ORGANISM: Artificial Sequence
<220> FEATURE:
<223> OTHER INFORMATION: Probe oligomer core sequence

<400> SEQUENCE: 38
gttgagctag                10

<210> SEQ ID NO 39
<211> LENGTH: 20
<212> TYPE: DNA
<213> ORGANISM: Artificial Sequence
<220> FEATURE:

<223> OTHER INFORMATION: Probe oligomer region

<400> SEQUENCE: 39
ggccgttgag ctagccagcg        20

<210> SEQ ID NO 40
<211> LENGTH: 45
<212> TYPE: DNA
<213> ORGANISM: Artificial Sequence
<220> FEATURE:
<223> OTHER INFORMATION: Probe oligomer region

<400> SEQUENCE: 40
ggccgttgag ctagccagcg agacgctgat gaagcgcgaa ctgac        45

<210> SEQ ID NO 41
<211> LENGTH: 45
<212> TYPE: RNA
<213> ORGANISM: Artificial Sequence
<220> FEATURE:
<223> OTHER INFORMATION: Probe oligomer region

<400> SEQUENCE: 41
ggccguugag cuagccagcg agacgcugau gaagcgcgaa cugac        45

<210> SEQ ID NO 42
<211> LENGTH: 14
<212> TYPE: DNA
<213> ORGANISM: Artificial Sequence
<220> FEATURE:
<223> OTHER INFORMATION: Amp oligomer core sequence

<400> SEQUENCE: 42
tgggtttggc ggtc        14

<210> SEQ ID NO 43
<211> LENGTH: 29
<212> TYPE: DNA
<213> ORGANISM: Artificial Sequence
<220> FEATURE:
<223> OTHER INFORMATION: Amp oligomer region

<400> SEQUENCE: 43
cgaacgtggt gggtttggcg gtctcgtcc        29

<210> SEQ ID NO 44
<211> LENGTH: 10
<212> TYPE: DNA
<213> ORGANISM: Artificial Sequence
<220> FEATURE:
<223> OTHER INFORMATION: Amp oligomer core sequence

<400> SEQUENCE: 44
agctgcgcct        10

<210> SEQ ID NO 45
<211> LENGTH: 28
<212> TYPE: DNA
<213> ORGANISM: Artificial Sequence
<220> FEATURE:
<223> OTHER INFORMATION: Amp oligomer region

<400> SEQUENCE: 45
ccgacgtcca gctgcgcctc acgaagcc        28

```
<210> SEQ ID NO 46
<211> LENGTH: 11
<212> TYPE: DNA
<213> ORGANISM: Artificial Sequence
<220> FEATURE:
<223> OTHER INFORMATION: Probe oligomer core sequence

<400> SEQUENCE: 46
gaaggtggtg a                                                              11

<210> SEQ ID NO 47
<211> LENGTH: 27
<212> TYPE: DNA
<213> ORGANISM: Artificial Sequence
<220> FEATURE:
<223> OTHER INFORMATION: Probe oligomer region

<400> SEQUENCE: 47
cagctcacga aggtggtgaa cgccgtc                                             27

<210> SEQ ID NO 48
<211> LENGTH: 11
<212> TYPE: DNA
<213> ORGANISM: Artificial Sequence
<220> FEATURE:
<223> OTHER INFORMATION: Amp oligomer core sequence

<400> SEQUENCE: 48
gtgcgcgcgt t                                                              11

<210> SEQ ID NO 49
<211> LENGTH: 28
<212> TYPE: DNA
<213> ORGANISM: Artificial Sequence
<220> FEATURE:
<223> OTHER INFORMATION: Amp oligomer region

<400> SEQUENCE: 49
ggtgacgcag gtgcgcgcgt taaacacg                                            28

<210> SEQ ID NO 50
<211> LENGTH: 14
<212> TYPE: DNA
<213> ORGANISM: Artificial Sequence
<220> FEATURE:
<223> OTHER INFORMATION: Amp oligomer core sequence

<400> SEQUENCE: 50
gaccgccaaa ccca                                                           14

<210> SEQ ID NO 51
<211> LENGTH: 29
<212> TYPE: DNA
<213> ORGANISM: Artificial Sequence
<220> FEATURE:
<223> OTHER INFORMATION: Amp oligomer region

<400> SEQUENCE: 51
ggacgagacc gccaaaccca ccacgttcg                                           29

<210> SEQ ID NO 52
<211> LENGTH: 10
<212> TYPE: DNA
<213> ORGANISM: Artificial Sequence
<220> FEATURE:
<223> OTHER INFORMATION: Probe oligomer core sequence
```

```
<400> SEQUENCE: 52
ccccaacggc                                                                  10

<210> SEQ ID NO 53
<211> LENGTH: 25
<212> TYPE: RNA
<213> ORGANISM: Artificial Sequence
<220> FEATURE:
<223> OTHER INFORMATION: Probe oligomer region

<400> SEQUENCE: 53
agcucggccc caacggcaag uuuuc                                                 25

<210> SEQ ID NO 54
<211> LENGTH: 27
<212> TYPE: DNA
<213> ORGANISM: Artificial Sequence
<220> FEATURE:
<223> OTHER INFORMATION: T7 promoter sequence
<220> FEATURE:
<221> NAME/KEY: promoter
<222> LOCATION: (1)..(27)

<400> SEQUENCE: 54
aatttaatac gactcactat aggaga                                                27

<210> SEQ ID NO 55
<211> LENGTH: 48
<212> TYPE: DNA
<213> ORGANISM: Artificial Sequence
<220> FEATURE:
<223> OTHER INFORMATION: Synthetic Oligo
<220> FEATURE:
<221> NAME/KEY: promoter
<222> LOCATION: (1)..(27)

<400> SEQUENCE: 55
aatttaatac gactcactat agggagaaat cggaggcctg ggagtaac                        48

<210> SEQ ID NO 56
<211> LENGTH: 19
<212> TYPE: DNA
<213> ORGANISM: Artificial Sequence
<220> FEATURE:
<223> OTHER INFORMATION: Synthetic Oligo

<400> SEQUENCE: 56
atcaatctcg ccgccagct                                                        19

<210> SEQ ID NO 57
<211> LENGTH: 23
<212> TYPE: DNA
<213> ORGANISM: Artificial Sequence
<220> FEATURE:
<223> OTHER INFORMATION: Synthetic Oligo

<400> SEQUENCE: 57
cacaaccttt ggatccggaa ggc                                                   23

<210> SEQ ID NO 58
<211> LENGTH: 49
<212> TYPE: DNA
<213> ORGANISM: Artificial Sequence
<220> FEATURE:
<223> OTHER INFORMATION: Synthetic Oligo
<220> FEATURE:
<221> NAME/KEY: promoter
```

<222> LOCATION: (1)..(27)

<400> SEQUENCE: 58
aatttaatac gactcactat agggagaatc ggaggcctgg gagtaacgg                49

<210> SEQ ID NO 59
<211> LENGTH: 23
<212> TYPE: DNA
<213> ORGANISM: Artificial Sequence
<220> FEATURE:
<223> OTHER INFORMATION: Synthetic Oligo

<400> SEQUENCE: 59
cacaaccttt ggatccggaa ggc                                           23

<210> SEQ ID NO 60
<211> LENGTH: 20
<212> TYPE: DNA
<213> ORGANISM: Artificial Sequence
<220> FEATURE:
<223> OTHER INFORMATION: Synthetic Oligo

<400> SEQUENCE: 60
tacccccgta gcgatgggca                                               20

<210> SEQ ID NO 61
<211> LENGTH: 52
<212> TYPE: DNA
<213> ORGANISM: Artificial Sequence
<220> FEATURE:
<223> OTHER INFORMATION: Synthetic Oligo
<220> FEATURE:
<221> NAME/KEY: promoter
<222> LOCATION: (1)..(27)

<400> SEQUENCE: 61
aatttaatac gactcactat agggagaaga ggacggacgg ataggaggcc tg           52

<210> SEQ ID NO 62
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 62
taaatctcgc cgcccgctca c                                             21

<210> SEQ ID NO 63
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 63
gaagcccggg ccgtcgtcac t                                             21

<210> SEQ ID NO 64
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 64
aaatctcgcc gcccgctcac c                                          21

<210> SEQ ID NO 65
<211> LENGTH: 22
<212> TYPE: DNA
<213> ORGANISM: Artificial Sequence
<220> FEATURE:
<223> OTHER INFORMATION: Synthetic Oligo

<400> SEQUENCE: 65
ggaagcccgg gccgtcgtca ct                                         22

<210> SEQ ID NO 66
<211> LENGTH: 50
<212> TYPE: DNA
<213> ORGANISM: Artificial Sequence
<220> FEATURE:
<223> OTHER INFORMATION: Synthetic Oligo
<220> FEATURE:
<221> NAME/KEY: promoter
<222> LOCATION: (1)..(27)

<400> SEQUENCE: 66
aatttaatac gactcactat agggagaacg ccttaccaga ggacggacgg            50

<210> SEQ ID NO 67
<211> LENGTH: 26
<212> TYPE: DNA
<213> ORGANISM: Artificial Sequence
<220> FEATURE:
<223> OTHER INFORMATION: Synthetic Oligo

<400> SEQUENCE: 67
gacagcgagc tgtacgcgga ctggag                                     26

<210> SEQ ID NO 68
<211> LENGTH: 21
<212> TYPE: DNA
<213> ORGANISM: Artificial Sequence
<220> FEATURE:
<223> OTHER INFORMATION: Synthetic Oligo

<400> SEQUENCE: 68
gcctcgtctt cgctttccga g                                          21

<210> SEQ ID NO 69
<211> LENGTH: 53
<212> TYPE: DNA
<213> ORGANISM: Artificial Sequence
<220> FEATURE:
<223> OTHER INFORMATION: Synthetic Oligo

<400> SEQUENCE: 69
ugggugcugg ugcuggacga tttaaaaaaa aaaaaaaaa aaaaaaaaaa aaa         53

<210> SEQ ID NO 70
<211> LENGTH: 20
<212> TYPE: RNA
<213> ORGANISM: Artificial Sequence
<220> FEATURE:
<223> OTHER INFORMATION: Synthetic Oligo

<400> SEQUENCE: 70
ugggugcugg ugcuggacga                                            20

<210> SEQ ID NO 71

```
<211> LENGTH: 53
<212> TYPE: DNA
<213> ORGANISM: Artificial Sequence
<220> FEATURE:
<223> OTHER INFORMATION: Synthetic Oligo

<400> SEQUENCE: 71
accugggugc uggugcugga tttaaaaaaa aaaaaaaaaa aaaaaaaaaa aaa    53

<210> SEQ ID NO 72
<211> LENGTH: 20
<212> TYPE: RNA
<213> ORGANISM: Artificial Sequence
<220> FEATURE:
<223> OTHER INFORMATION: Synthetic Oligo

<400> SEQUENCE: 72
accugggugc uggugcugga                                         20

<210> SEQ ID NO 73
<211> LENGTH: 17
<212> TYPE: RNA
<213> ORGANISM: Artificial Sequence
<220> FEATURE:
<223> OTHER INFORMATION: Synthetic Oligo

<400> SEQUENCE: 73
ugggugcugg ugcugga                                            17

<210> SEQ ID NO 74
<211> LENGTH: 23
<212> TYPE: RNA
<213> ORGANISM: Artificial Sequence
<220> FEATURE:
<223> OTHER INFORMATION: Synthetic Oligo

<400> SEQUENCE: 74
accugggugc uggugcugga cga                                     23

<210> SEQ ID NO 75
<211> LENGTH: 11
<212> TYPE: RNA
<213> ORGANISM: Artificial Sequence
<220> FEATURE:
<223> OTHER INFORMATION: Synthetic Oligo

<400> SEQUENCE: 75
gugcuggugc u                                                  11

<210> SEQ ID NO 76
<211> LENGTH: 30
<212> TYPE: RNA
<213> ORGANISM: Artificial Sequence
<220> FEATURE:
<223> OTHER INFORMATION: Synthetic Oligo

<400> SEQUENCE: 76
aucuggaccu gggugcuggu gcuggacgac                              30
```

COMPOSITIONS, METHODS AND KITS TO DETECT HERPES SIMPLEX VIRUS NUCLEIC ACIDS

PRIORITY

This application is a Continuation of U.S. patent application Ser. No. 16/046,429, filed Jul. 26, 2018, which is a Continuation of U.S. patent application Ser. No. 15/487,240, filed Apr. 13, 2017, which is a Divisional of U.S. patent application Ser. No. 14/395,039, filed Oct. 16, 2014, which is a National Stage Entry under 35 U.S.C. § 371 of PCT Patent Application No. PCT/US2013/037808, filed Apr. 23, 2013, which claims the benefit of priority to the following applications: U.S. Provisional Application No. 61/637,769 filed 24 Apr. 2012; U.S. Provisional Application No. 61/748,854 filed 4 Jan. 2013; and U.S. Provisional Application No. 61/773,718 filed 6 Mar. 2013. The entire contents of each of these priority documents are incorporated herein by reference.

SEQUENCE LISTING

The present application is filed with a Sequence Listing in electronic format. The Sequence Listing is provided as a file entitled "2019-10-09_01159-0036-02US_Seq_List_ST25.txt" created on Oct. 9, 2019, which is 19 KB in size. The information in the electronic format of the sequence listing is incorporated herein by reference in its entirety.

FIELD

The present invention relates to the detection of infectious agents, more specifically to the detection of Herpes Simplex virus (HSV). Compositions, methods and kits are described for the detection of HSV (including HSV types 1 and 2) by using in vitro nucleic acid amplification techniques.

BACKGROUND

Herpes simplex virus (HSV) is part of the larger herpes virus family, including Varicella-Zoster virus (VZV), Epstein-Barr virus (EBV) and Cytomegalovirus (CMV). It is an enveloped double-stranded DNA virus causing infections in humans. HSV is classified into various types, including HSV-1 and HSV-2. The complete genomes of human HSV-1 and HSV-2 have been sequenced (see, e.g., NCBI Accession Nos. NC_001806.1/GI:9629378 and NC_001798.1/GI:9629267, respectively; see also accession numbers X14112 and Z86099, respectively). Both HSV-1 and HSV-2 can cause disease in humans and exposure or infection is fairly common in adult populations. Up to 80% of the U.S. adult population has been exposed to HSV-1 and approximately 20% of the U.S. population has contracted HSV-2 infections.

HSV infection symptoms include the common cold sore found near the lips and also genital herpes. The virus can also cause keratoconjunctivitis, with the potential to lead to blindness, and encephalitis. Once subsided, the virus remains in a latent state inside nerve cells (ganglia) that supply nerve fibres to the infected area. The virus can become reactivated and travels through the nerve fibres back to the skin, thereby causing recurrent disease.

HSV-2 is commonly associated with newborn encephalitis where it is associated with maternal genital infections. HSV-related encephalitis has the highest fatality rate of all types of encephalitis with an annual incidence of 1 to 4 per million. HSV encephalitis affects people of all ages and at any time of the year. In adults, HSV-related encephalitis is thought to be due to a reactivation of a latent virus. Symptoms may include fever, headaches, seizures, an altered level of consciousness and personality changes. The similarity of these symptoms to other maladies makes clinical diagnosis difficult. If left untreated, the mortality rate for Herpes Simplex Encephalitis (HSE) is as high as seventy percent, compared with as low as nineteen percent among those who receive treatment. Of the treated patients, about one third can return to normal function.

One mechanism for transmission of HSV is by sexual transmission. This route of transmission presents a serious consequence of HSV infection in the transmission of the HIV virus. HIV transmission is five times more likely to occur from an HIV/HSV-2-coinfected person with genital ulceration and HIV acquisition is twice as likely in someone sero-positive for HSV-2.

Accurate diagnosis of HSV infection is essential if transmission rates of HSV and its consequences are to be reduced. Although it is not possible to eradicate HSVs from an infected individual, episodic treatment with nucleoside analogue drugs will shorten the duration of the clinical episode and can also reduce the risk of transmission of the virus when continuously administered as daily suppressive therapy. Clinical diagnosis of HSV infection has been reported to have a poor sensitivity of only approximately 40% (*Expert Rev. Mol. Diagn.* 4, 485-493 (2004); *Sex. Trans. Dis.* 17, 90-94 (1990)) so rapid reliable tests with good sensitivity and specificity are needed to improve diagnostic accuracy in those with and without symptoms. Tests are also required that differentiate between HSV-1 and -2.

Current diagnostic methods for HSV include viral culture, serological tests and nucleic acid amplification testing (NAAT).

Culture and typing were once considered the gold standard for diagnosis but its usefulness is severely limited by the stage of clinical disease. When testing early vesicular lesions, the culture detection rate is about 90% whereas in older crusted lesions this falls to only 27% (*Genitourin. Med.* 64, 103-106 (1988)). Another problem with this method is that it is slow since it takes 3 days for the majority of culture isolates to appear positive. The liability of the virus also means that samples must be transported rapidly with maintenance of the cold chain otherwise much reduced sensitivity will result due to, for example, bacterial outgrowth.

Detection of HSV infections has improved dramatically with the advent of type-specific HSV antibody serology testing (*Am. J. Clin. Pathol.* 120, 829-844 (2003). These tests are sensitive and can distinguish between HSV-1 and HSV-2 antibodies. However, type specific antibody tests suffer from false positive results and are also considered inadequate due to a delay of between two and three weeks in appearance of antibody response after initial infection. The performance of the same test can also vary, giving different sensitivities and specificities depending on the population tested (*Clin. Microbiol. Infect.* 10, 530-536 (2004)). For these reasons, they are not considered suitable for general population screening.

NAAT testing for HSV provides for the direct detection of viral DNA from specimens by amplifying DNA sequences using HSV-1 or -2 specific primers and has been shown to be superior to culture (*Sex. Trans. Infect.* 78, 21-25 (2002); *Sex. Trans. Infect.* 80, 406-410 (2004)) and highly specific as compared to cell culture (*J. Infect. Dis.* 1345-1351(2003)). Different HSV genes have been identified as targets for DNA amplification, among them, DNA polymerase glycoprotein. NAAT based testing for HSV has utilised Strand-displacement amplification (SDA), PCR, real time PCR and the TaqMan® PCR detection system. NAAT based assays for HSV are now considered to be the gold standard. However, PCR-based amplification assays are not without their limitations. For example, tests may take up to 2 days to complete and require specialized thermo-cycling equipment.

Sciortino et al. (2001) *J. Virol.* 75, 17 pp. 8105-8116 describe a method for the detection of HSV using reverse transcribed RNAs that were detected by PCR. A set of 90 primers were designed to amplify all of the 84 expressed ORFs of HSV. One primer pair was designed to amplify a portion of the UL42 ORF of HSV-1, hybridising to regions 301 to 322 and 680 to 701 of GenBank Accession No: GU734771.1, GI:290766003, region 92815 . . . 94534. However, the method described therein suffers from the problems associated with PCR-based amplification methodologies and also requires a reverse transcription step which adds yet further complexity to the method. It is also believed that this assay would not be able to discriminate between HSV-1 and HSV-2 nucleic acids.

A need remains for a diagnostic test that provides sensitive and specific detection of HSV in a relatively short time so that infected individuals may be treated promptly to limit morbidity and prevent the spread of infection. A test of this kind that distinguishes between HSV-1 and/or HSV-2 would also be desirable and so a type determination of HSV that is present in the sample can be made.

SUMMARY

The present invention relates to methods, compositions, kits and nucleic acids for determining the presence of HSV, specifically HSV-1 and/or HSV-2, in a sample. The methods involve the amplification of viral nucleic acid to detect the HSV target sequence in the sample. The methods can advantageously provide for the sensitive detection and type-determination of HSV. The present invention is also directed to a method—such as a TMA based method—for the detection of HSV which provides for the direct, rapid, specific and sensitive detection of HSV RNA. Targeting single stranded RNA is beneficial over targeting the double stranded genomic DNA because there is no need for an additional denaturation step which otherwise adds further complexity to the method. The use of RNA can also provide improved amplification oligomer efficiency when methods—such as TMA—start from a single stranded nucleic acid molecule. A distinct viral RNA expressed in infected cells and packaged by HSV-1 and HSV-2 virions, UL42, was selected as a target for amplification and detection. (Georgopoulou, *J. Virol.* 67, 3961, (1993); McGeoch, *J. Gen. Virol.* 69, 1531, (1988); Sciortino et al. *PNAS* 99, 12, 8318, (2002); and Sciortino, *J. Virol.* 75, 8105, (2001)).

A viral nucleic acid that is targeted according to the present invention is the UL42 open reading frame (ORF) of HSV. This ORF is present in both HSV-1 and HSV-2. The nucleic acid sequence of the UL42 ORF in HSV-1 is different than the UL42 ORF nucleic acid sequence in HSV-2. This difference in nucleic acid sequences can be exploited by designing amplification oligomers and/or nucleic acid probes that are specific for each of the sequences. Thus, the methods of the present invention can be used to distinguish between the two types of HSV. Accordingly, it is possible to determine if a sample comprises HSV-1 or HSV-2 or a combination thereof. Accordingly, it is possible to determine if a sample comprises HSV-1 or HSV-2 or a combination thereof in both early and late stages of the viral lifecycle.

DNA sequences encoding the UL42 ORF from HSV-1 (SEQ ID NO:1) and HSV-2 (SEQ ID NO:2) are shown in Table 17. FIGS. 1A-C and 2A-B further illustrate the UL42 ORF from HSV-1 and HSV-2, respectively. Methods herein target the RNA sequences of SEQ ID NO:1 and 2. Methods herein may also target the DNA sequence of SEQ ID NO:1. Methods herein may also target the DNA sequence of SEQ ID NO:2.

In one aspect, the present invention provides a method for determining the presence or absence of Herpes Simplex Virus 1 (HSV-1) in a sample. The method includes the step of (1) contacting a sample, suspected of containing HSV-1, with at least two oligomers for amplifying a target region of an HSV-1 target nucleic acid, where the at least two amplification oligomers include (a) a first amplification oligomer comprising a first target-hybridizing sequence that is from about 15 to about 27 contiguous nucleotides contained in the sequence of SEQ ID NO:31 and that includes at least the sequence of SEQ ID NO:30, and (b) a second amplification oligomer comprising a second target-hybridizing sequence that is from about 15 to about 27 contiguous nucleotides contained in the sequence of SEQ ID NO:33 and that includes at least the sequence of SEQ ID NO:32. The method further includes (2) performing an in vitro nucleic acid amplification reaction, where any HSV-1 target nucleic acid present in the sample is used as a template for generating an amplification product, and (3) detecting the presence or absence of the amplification product, thereby indicating the presence or absence of HSV-1 in the sample. In some variations, the first target-hybridizing sequence is contained in the sequence of SEQ ID NO:29 and/or includes at least the sequence of SEQ ID NO:28. Suitable first target-hybridizing sequences for the first amplification oligomer include SEQ ID NO:20, SEQ ID NO:6, and SEQ ID NO:12. Suitable second target-hybridizing sequences for the second amplification oligomer include SEQ ID NO:7 and SEQ ID NO:9. In more particular variations, the first and second target-hybridizing sequences respectively have the nucleotide sequences of (i) SEQ ID NO:20 and SEQ ID NO:7, (ii) SEQ ID NO:6 and SEQ ID NO:7, or (iii) SEQ ID NO:6 and SEQ ID NO:9.

In some embodiments of a method for determing the presence or absence of HSV-1, the first amplification oligomer is a promoter primer or promoter provider further comprising a promoter sequence located 5' to the first target-hybridizing sequence. A particularly suitable promoter sequence is a T7 promoter sequence such as, e.g., the nucleotide sequence of SEQ ID NO:54. In some such variations, the first amplification oligomer has a sequence selected from SEQ ID NO:19, SEQ ID NO:5, and SEQ ID NO:11.

In certain embodiments, the detecting step (3) includes contacting the in vitro nucleic acid amplification reaction with a detection probe oligomer configured to specifically hybridize to the amplification product under conditions whereby the presence or absence of the amplification product is determined, thereby indicating the presence or absence of HSV-1 in the sample. Typically, the detection probe oligomer includes a target-hybridizing sequence that is from about 14 to about 40 nucleotides in length and is configured to specifically hybridize to a target sequence contained within SEQ ID NO:1 from about nucleotide position 635 to about nucleotide position 683. For example, the detection probe target-hybridizing sequence may be contained in the sequence of SEQ ID NO:40 or SEQ ID NO:41 and include at least the sequence of SEQ ID NO:34, SEQ ID NO:35, or SEQ ID NO:38.

In some embodiments of a detection probe target-hybridizing sequence that includes at least the sequence of SEQ ID NO:34 or SEQ ID NO:35, the target-hybridizing sequence is contained in the sequence of SEQ ID NO:36 or SEQ ID NO:37. In specific variations, the detection probe target-hybridizing sequence is SEQ ID NO:8 or SEQ ID NO:22; in some such variations, the first and second amplification oligomer target-hybridizing sequences respectively have the nucleotide sequences of (i) SEQ ID NO:20 and SEQ ID NO:7, (ii) SEQ ID NO:6 and SEQ ID NO:7, or (iii) SEQ ID NO:6 and SEQ ID NO:9.

In some embodiments of a detection probe target-hybridizing sequence that includes at least the sequence of SEQ ID NO:38, the detection probe target-hybridizing sequence is contained in the sequence of SEQ ID NO:39. In specific variations, the detection probe target-hybridizing sequence has the sequence of SEQ ID NO:10; in some such variations, the first and second amplification oligomer target-hybridizing sequences respectively have the nucleotide sequences of (i) SEQ ID NO:20 and SEQ ID NO:7, (ii) SEQ ID NO:6 and SEQ ID NO:7, or (iii) SEQ ID NO:6 and SEQ ID NO:9.

In one aspect, the present invention provides a method for determining the presence or absence of Herpes Simplex Virus 2 (HSV-2) in a sample. The method includes the step of (1) contacting a sample, suspected of containing HSV-2, with at least two oligomers for amplifying a target region of an HSV-2 target nucleic acid, where the at least two amplification oligomers include (a) a first amplification oligomer comprising a first target-hybridizing sequence that is from about 15 to about 27 contiguous nucleotides (i) contained in the sequence of SEQ ID NO:49 and that includes at least the sequence of SEQ ID NO:48 or (ii) contained in the sequence of SEQ ID NO:43 and that includes at least the sequence of SEQ ID NO:42; and (b) a second amplification oligomer comprising a second target-hybridizing sequence that is from about 15 to about 27 contiguous nucleotides (i) contained in the sequence of SEQ ID NO:51 and that includes at least the sequence of SEQ ID NO:50 or (ii) contained in the sequence of SEQ ID NO:45 and that includes at least the sequence of SEQ ID NO:44. The method further includes (2) performing an in vitro nucleic acid amplification reaction, where any HSV-2 target nucleic acid present in the sample is used as a template for generating an amplification product, and (3) detecting the presence or absence of the amplification product, thereby indicating the presence or absence of HSV-2 in the sample. In some embodiments, the first target hybridizing sequence is contained in the sequence of SEQ ID NO:49 and includes at least the sequence of SEQ ID NO:48, and the second target hybridizing sequence is contained in the sequence of SEQ ID NO:51 and includes at least the sequence of SEQ ID NO:50. In particular variations, the first target-hybridizing sequence has the sequence of SEQ ID NO:24 and/or the second target hybridizing sequence has the sequence of SEQ ID NO:25. In other embodiments, the first target hybridizing sequence is contained in the sequence of SEQ ID NO:43 and includes at least the sequence of SEQ ID NO:42, and the second target hybridizing sequence is contained in the sequence of SEQ ID NO:45 and includes at least the sequence of SEQ ID NO:44. In particular variations, the first target-hybridizing sequence has the sequence of SEQ ID NO:14 and/or the second target hybridizing sequence has the sequence of SEQ ID NO:15.

In some embodiments of a method for determing the presence or absence of HSV-2, the first amplification oligomer is a promoter primer or promoter provider further comprising a promoter sequence located 5' to the first target-hybridizing sequence. A particularly suitable promoter sequence is a T7 promoter sequence such as, e.g., the nucleotide sequence of SEQ ID NO:54. In some such variations, the first amplification oligomer has a sequence selected from SEQ ID NO:23 and SEQ ID NO:13.

In certain embodiments of a method for determining the presence or absence of HSV-2, the detecting step (3) includes contacting the in vitro nucleic acid amplification reaction with a detection probe oligomer configured to specifically hybridize to the amplification product under conditions whereby the presence or absence of the amplification product is determined, thereby indicating the presence or absence of HSV-2 in the sample. In some embodiments—where the first target hybridizing sequence is contained in the sequence of SEQ ID NO:49 and includes at least the sequence of SEQ ID NO:48, and the second target hybridizing sequence is contained in the sequence of SEQ ID NO:51 and includes at least the sequence of SEQ ID NO:50—the detection probe oligomer includes a target-hybridizing sequence that is from about 14 to about 25 nucleotides in length and configured to specifically hybridize to a target sequence contained within SEQ ID NO:2 from about nucleotide position 608 to about nucleotide position 632. In certain variations, the detection probe target-hybridizing sequence is contained in the sequence of SEQ ID NO:53 and includes at least the sequence of SEQ ID NO:52. A particularly suitable detection probe target-hybridizing sequence has the sequence of SEQ ID NO:27; in some such variations, the first and second amplification oligomer target-hybridizing sequences have the nucleotide sequences of SEQ ID NO:24 and SEQ ID NO:25, respectively.

In other embodiments of a method for determining the presence or absence of HSV-2 comprising the use of a detection probe—where the first target hybridizing sequence is contained in the sequence of SEQ ID NO:43 and includes at least the sequence of SEQ ID NO:42, and the second target hybridizing sequence is contained in the sequence of SEQ ID NO:45 and includes at least the sequence of SEQ ID NO:44—the detection probe oligomer includes a target-hybridizing sequence that is from about 14 to about 30 nucleotides in length and configured to specifically hybridize to a target sequence contained within SEQ ID NO:2 from about nucleotide position 549 to about nucleotide position 578. In certain variations, the detection probe target-hybridizing sequence is contained in the sequence of SEQ ID NO:47 and includes at least the sequence of SEQ ID NO:46. A particularly suitable detection probe target-hybridizing sequence has the sequence of SEQ ID NO:16; in some such variations, the first and second amplification oligomer target-hybridizing sequences have the nucleotide sequences of SEQ ID NO:14 and SEQ ID NO:15, respectively.

Typically, a method for determining the presence or absence of HSV-1 or HSV-2 as above further includes purifying the HSV-1 or HSV-2 target nucleic acid from other components in the sample before step (1). In particular embodiments, the purifying step includes contacting the sample with at least one capture probe oligomer comprising a target-hybridizing sequence covalently attached to a sequence or moiety that binds to an immobilized probe. Suitable target-hybridizing sequences include SEQ ID NO:4, SEQ ID NO:18, SEQ ID NO:70, and SEQ ID NO:72. In more particular variations, the capture probe oligomer has a sequence selected from SEQ ID NO:3, SEQ ID NO:17, SEQ ID NO:69, and SEQ ID NO:71.

In certain embodiments in which the purifying step includes contacting the sample with at least one capture probe oligomer comprising a target-hybridizing sequence covalently attached to a sequence or moiety that binds to an immobilized probe, the target-hybridizing sequence is from about 15 to about 30 contiguous nucleotides contained in the sequence of SEQ ID NO:76 and includes at least the sequence of SEQ ID NO:75. In some variations, the capture probe target-hybridizing sequence is contained in the sequence of SEQ ID NO:74 and/or includes at least the sequence of SEQ ID NO:75. Particularly suitable target-hybridizing sequences include SEQ ID NO:70 and SEQ ID NO:72. In some embodiments, the purifying step further includes contacting the sample with a second capture probe oligomer comprising a target-hybridizing sequence configured to specifically hybridize to the HSV-1 and/or HSV-2 target nucleic acid, where the second capture probe target-hybridizing sequence is covalently attached to a sequence or moiety that binds to an immobilized probe; in some such variations, the second capture probe oligomer has a target-hybridizing sequence as shown in SEQ ID NO:4 or SEQ ID NO:18.

In some embodiments of a method as above for determining the presence or absence of HSV-1 or HSV-2 utilizing a detection probe oligomer, the detection probe includes at least one label. In specific variations, the label is a chemiluminescent label or a fluorescent label. In some embodiments utilizing a labeled detection probe, the detecting step (3) occurs during the amplifying step (2). Particularly suitable detection probes that may comprise a fluorescent label and a quencher include a molecular torch, a molecular beacon, and a TaqMan detection probe.

In still other embodiments of a method utilizing a detection probe oligomer, the detection probe further includes a non-target-hybridizing sequence. In particular embodiments, a detection probe comprising a non-target-hybridizing sequence is a hairpin detection probe such as, e.g., a molecular torch or a molecular beacon.

In certain embodiments of a method for determining the presence or absence of HSV-1 or HSV-2 as above, the amplification reaction at step (2) is an isothermal amplification reaction or a PCR amplification reaction. In specific variations, the isothermal amplification reaction is a transcription-mediated amplification (TMA) reaction. In some embodiments of a method utilizing an isothermal or PCR amplification reaction, the reaction is a real-time amplification reaction.

In another aspect, the present invention provides a combination of at least two oligomers for determining the presence or absence of Herpes Simplex Virus 1 (HSV-1) in a sample. The oligomer combination includes first and second amplification oligomers for amplifying a target region of an HSV-1 target nucleic acid, where (a) the first amplification oligomer comprises a first target-hybridizing sequence that is from about 15 to about 27 contiguous nucleotides contained in the sequence of SEQ ID NO:31 and that includes at least the sequence of SEQ ID NO:30, and (b) the second amplification oligomer comprises a second target-hybridizing sequence that is from about 15 to about 27 contiguous nucleotides contained in the sequence of SEQ ID NO:33 and that includes at least the sequence of SEQ ID NO:32. In some variations, the first target-hybridizing sequence is contained in the sequence of SEQ ID NO:29 and/or includes at least the sequence of SEQ ID NO:28. Suitable first target-hybridizing sequences for the first amplification oligomer include SEQ ID NO:20, SEQ ID NO:6, and SEQ ID NO:12. Suitable second target-hybridizing sequences for the second amplification oligomer include SEQ ID NO:7 and SEQ ID NO:9. In more particular variations, the first and second target-hybridizing sequences respectively have the nucleotide sequences of (i) SEQ ID NO:20 and SEQ ID NO:7, (ii) SEQ ID NO:6 and SEQ ID NO:7, or (iii) SEQ ID NO:6 and SEQ ID NO:9.

In some embodiments of an oligomer combination for determining the presence or absence of HSV-1, the first amplification oligomer is a promoter primer or promoter provider further comprising a promoter sequence located 5' to the first target-hybridizing sequence. A particularly suitable promoter sequence is a T7 promoter sequence such as, e.g., the nucleotide sequence of SEQ ID NO:54. In some such variations, the first amplification oligomer has a sequence selected from SEQ ID NO:19, SEQ ID NO:5, and SEQ ID NO:11.

In certain embodiments, an oligomer combination for determining the presence or absence of HSV-1 as above further includes a detection probe oligomer. Typically, the detection probe oligomer includes a target-hybridizing sequence that is from about 14 to about 40 nucleotides in length and is configured to specifically hybridize to a target sequence contained within SEQ ID NO:1 from about nucleotide position 635 to about nucleotide position 683. For example, the detection probe target-hybridizing sequence may be contained in the sequence of SEQ ID NO:40 or SEQ ID NO:41 and include at least the sequence of SEQ ID NO:34, SEQ ID NO:35, or SEQ ID NO:38.

In some embodiments of a detection probe target-hybridizing sequence that includes at least the sequence of SEQ ID NO:34 or SEQ ID NO:35, the target-hybridizing sequence is contained in the sequence of SEQ ID NO:36 or SEQ ID NO:37. In specific variations, the detection probe target-hybridizing sequence is SEQ ID NO:8 or SEQ ID NO:22; in some such variations, the first and second amplification oligomer target-hybridizing sequences respectively have the nucleotide sequences of (i) SEQ ID NO:20 and SEQ ID NO:7, (ii) SEQ ID NO:6 and SEQ ID NO:7, or (iii) SEQ ID NO:6 and SEQ ID NO:9.

In some embodiments of a detection probe target-hybridizing sequence that includes at least the sequence of SEQ ID NO:38, the detection probe target-hybridizing sequence is contained in the sequence of SEQ ID NO:39. In specific variations, the detection probe target-hybridizing sequence has the sequence of SEQ ID NO:10; in some such variations, the first and second amplification oligomer target-hybridizing sequences respectively have the nucleotide sequences of (i) SEQ ID NO:20 and SEQ ID NO:7, (ii) SEQ ID NO:6 and SEQ ID NO:7, or (iii) SEQ ID NO:9 and SEQ ID NO:9.

In another aspect, the present invention provides a combination of at least two oligomers for determining the presence or absence of Herpes Simplex Virus 2 (HSV-2) in a sample. The oligomer combination includes first and second amplification oligomers for amplifying a target region of an HSV-2 target nucleic acid, where (a) a first amplification oligomer comprising a first target-hybridizing sequence that is from about 15 to about 27 contiguous nucleotides (i) contained in the sequence of SEQ ID NO:49 and that includes at least the sequence of SEQ ID NO:48 or (ii) contained in the sequence of SEQ ID NO:43 and that includes at least the sequence of SEQ ID NO:42; and (b) a second amplification oligomer comprising a second target-hybridizing sequence that is from about 15 to about 27 contiguous nucleotides (i) contained in the sequence of SEQ ID NO:51 and that includes at least the sequence of SEQ ID NO:50 or (ii) contained in the sequence of SEQ ID NO:45 and that includes at least the sequence of SEQ ID NO:44. In some embodiments, the first target hybridizing sequence is contained in the sequence of SEQ ID NO:49 and includes at least the sequence of SEQ ID NO:48, and the second target hybridizing sequence is contained in the sequence of SEQ ID NO:51 and includes at least the sequence of SEQ ID NO:50. In particular variations, the first target-hybridizing sequence has the sequence of SEQ ID NO:24 and/or the second target hybridizing sequence has the sequence of SEQ ID NO:25. In other embodiments, the first target hybridizing sequence is contained in the sequence of SEQ ID NO:43 and includes at least the sequence of SEQ ID NO:42, and the second target hybridizing sequence is contained in the sequence of SEQ ID NO:45 and includes at least the sequence of SEQ ID NO:44. In particular variations, the first target-hybridizing sequence has the sequence of SEQ ID NO:14 and/or the second target hybridizing sequence has the sequence of SEQ ID NO:15.

In some embodiments of an oligomer combination for determining the presence or absence of HSV-2, the first amplification oligomer is a promoter primer or promoter provider further comprising a promoter sequence located 5' to the first target-hybridizing sequence. A particularly suitable promoter sequence is a T7 promoter sequence such as, e.g., the nucleotide sequence of SEQ ID NO:54. In some such variations, the first amplification oligomer has a sequence selected from SEQ ID NO:23 and SEQ ID NO:13.

In certain embodiments, an oligomer combination for determining the presence or absence of HSV-2 as above further includes a detection probe oligomer. In some embodiments—where the first target hybridizing sequence is contained in the sequence of SEQ ID NO:49 and includes at least the sequence of SEQ ID NO:48, and the second target hybridizing sequence is contained in the sequence of SEQ ID NO:51 and includes at least the sequence of SEQ ID NO:50—the detection probe oligomer includes a target-hybridizing sequence that is from about 14 to about 25 nucleotides in length and configured to specifically hybridize to a target sequence contained within SEQ ID NO:2 from about nucleotide position 608 to about nucleotide position 632. In certain variations, the detection probe target-hybridizing sequence is contained in the sequence of SEQ ID NO:53 and includes at least the sequence of SEQ ID NO:52. A particularly suitable detection probe target-hybridizing sequence has the sequence of SEQ ID NO:27; in some such variations, the first and second amplification oligomer target-hybridizing sequences have the nucleotide sequences of SEQ ID NO:24 and SEQ ID NO:25, respectively.

In other embodiments of an oligomer combination for determining the presence or absence of HSV-2 comprising a detection probe—where the first target hybridizing sequence is contained in the sequence of SEQ ID NO:43 and includes at least the sequence of SEQ ID NO:42, and the second target hybridizing sequence is contained in the sequence of SEQ ID NO:45 and includes at least the sequence of SEQ ID NO:44—the detection probe oligomer includes a target-hybridizing sequence that is from about 14 to about 30 nucleotides in length and configured to specifically hybridize to a target sequence contained within SEQ ID NO:2 from about nucleotide position 549 to about nucleotide position 578. In certain variations, the detection probe target-hybridizing sequence is contained in the sequence of SEQ ID NO:47 and includes at least the sequence of SEQ ID NO:46. A particularly suitable detection probe target-hybridizing sequence has the sequence of SEQ ID NO:16; in some such variations, the first and second amplification oligomer target-hybridizing sequences have the nucleotide sequences of SEQ ID NO:14 and SEQ ID NO:15, respectively.

An oligomer combination for determining the presence or absence of HSV-1 or HSV-2 as above may also include at least one capture probe oligomer. In some such embodiments, the capture probe oligomer includes a target-hybridizing sequence covalently attached to a sequence or moiety that binds to an immobilized probe. Suitable target-hybridizing sequences include SEQ ID NO:4, SEQ ID NO:18, SEQ ID NO:70, and SEQ ID NO:72. In more particular variations, the capture probe oligomer has a sequence selected from SEQ ID NO:3, SEQ ID NO:17, SEQ ID NO:69, and SEQ ID NO:71.

In certain embodiments in which the oligomer combination includes at least one capture probe oligomer comprising a target-hybridizing sequence covalently attached to a sequence or moiety that binds to an immobilized probe, the target-hybridizing sequence is from about 15 to about 30 contiguous nucleotides contained in the sequence of SEQ ID NO:76 and includes at least the sequence of SEQ ID NO:75. In some variations, the capture probe target-hybridizing sequence is contained in the sequence of SEQ ID NO:74 and/or includes at least the sequence of SEQ ID NO:75. Particularly suitable target-hybridizing sequences include SEQ ID NO:70 and SEQ ID NO:72. In some embodiments, the oligomer combination includes a second capture probe oligomer comprising a target-hybridizing sequence configured to specifically hybridize to the HSV-1 and/or HSV-2 target nucleic acid, where the second capture probe target-hybridizing sequence is covalently attached to a sequence or moiety that binds to an immobilized probe; in some such variations, the second capture probe oligomer has a target-hybridizing sequence as shown in SEQ ID NO:4 or SEQ ID NO:18.

In some embodiments of an oligomer combination as above for determining the presence or absence of HSV-1 or HSV-2 and comprising a detection probe oligomer, the detection probe includes at least one label. In specific variations, the label is a chemiluminescent label or a fluorescent label. In some embodiments, the detection probe includes a fluorescent label and a quencher. Particularly suitable detection probes that may comprise a fluorescent label and a quencher include a molecular torch, a molecular beacon, and a TaqMan detection probe.

In still other embodiments of an oligomer combination comprising a detection probe oligomer, the detection probe further includes a non-target-hybridizing sequence. In particular embodiments, a detection probe comprising a non-target-hybridizing sequence is a hairpin detection probe such as, e.g., a molecular torch or a molecular beacon.

In another aspect, the present invention provides a capture probe oligomer for isolating at least one of a HSV-1 target nucleic acid and HSV-2 target nucleic acid from a sample. In certain embodiments, the capture probe oligomer comprises a target-hybridizing sequence covalently attached to a sequence or moiety that binds to an immobilized probe, where the target-hybridizing sequence is from about 15 to about 30 contiguous nucleotides contained in the sequence of SEQ ID NO:76 and includes at least the sequence of SEQ ID NO:75. In some variations, the capture probe target-hybridizing sequence is contained in the sequence of SEQ ID NO:74 and/or includes at least the sequence of SEQ ID NO:75. Particularly suitable target-hybridizing sequences include SEQ ID NO:70 and SEQ ID NO:72.

In yet another aspect, the present invention provides a combination of at at least two oligomers for isolating at least one of a HSV-1 target nucleic acid and a HSV-2 target nucleic acid from a sample. In certain embodiments, the oligomer combination includes (1) a first capture probe oligomer comprising a first target-hybridizing sequence that is from about 15 to about 30 contiguous nucleotides contained in the sequence of SEQ ID NO:76 and includes at least the sequence of SEQ ID NO:75, and (2) a second capture probe oligomer comprising a second target-hybridizing sequence configured to specifically hybridize to at least one of the HSV-1 and HSV-2 target nucleic acids. Typically, each of the first and second target-hybridizing sequences is covalently attached to a sequence or moiety that binds to an immobilized probe. In some variations, the first capture probe target-hybridizing sequence is contained in the sequence of SEQ ID NO:74 and/or includes at least the sequence of SEQ ID NO:75. Particularly suitable first target-hybridizing sequences include SEQ ID NO:70 and SEQ ID NO:72. In some embodiments, the second capture probe target-hybridizing sequence is a sequence as shown in SEQ ID NO:4 or SEQ ID NO:18.

In other aspects, the present invention provides a kit or a reaction mixture comprising an oligomer combination as above.

These and other aspects of the invention will become evident upon reference to the following detailed description of the invention and the attached drawings.

BRIEF DESCRIPTION OF THE FIGURES

FIGS. 1A-C illustrate a reference sequence for the UL42 gene from a representative HSV-1 sequence (SEQ ID NO:1). Nucleotide positions 92,815-94,534 of GenBank Accession No. GU734771.1 (GI:290766003) are shown. (>gb|GU734771.1|:92815-94534 Human herpesvirus 1 strain F, complete genome).

FIGS. 2A-B illustrate a reference sequence for the UL42 gene from a representative HSV-2 sequence (SEQ ID NO:2). Nucleotide positions 93,769-95,181 of GenBank Accession No. Z86099.2 (GI:6572414) are shown. (>gi|6572414: 93769-95181 Herpes simplex virus type 2 (strain HG52), complete genome).

DETAILED DESCRIPTION

I. Overview

Nucleic acid oligomer sequences are disclosed that may serve as amplification oligomers for amplification of HSV nucleic acids, including HSV-1 and/or HSV-2 nucleic acids. An HSV nucleic acid may be detected in a sample by using a method of in vitro nucleic acid amplification, preferably by using a transcription-mediated amplification reaction such as TMA or NASBA, and detection of an amplified nucleic acid sequence, optionally using a detection probe. A detection probe hybridizes specifically to a portion of the amplified viral sequence, either after completion of or during the amplification process. In one embodiment, the detection probes hybridizes specifically to a portion of the amplified HSV-1 or HSV-2 sequence, either after completion of or during the amplification process. In particular variations, a detection probe is able to discriminate between HSV-1 and HSV-2 nucleic acids and so it is possible to determine if either HSV-1 and/or HSV-2 nucleic acid is present in the sample under test. Some embodiments detect the amplified products by using a homogeneous detection method that detects, in a mixture, a labeled probe bound specifically to an amplified sequence (see, e.g., Arnold et al., 1989, *Clin. Chem.* 35:1588-1594; U.S. Pat. No. 5,658,737, Nelson et al., and U.S. Pat. Nos. 5,118,801 and 5,312,728, Lizardi et al.).

Embodiments of the methods also use oligonucleotide sequences that serve as capture probes for processing a sample to capture the target HSV nucleic acid and separate it from other sample components (see, e.g., U.S. Pat. Nos. 6,110,678, 6,280,952 and 6,534,273).

Methods disclosed herein can be used to detect HSV nucleic acids present in samples from or derived from animals and humans, preferably from biopsies of genital lesions, anogenital lesions, oral lesions, mucocutanoeus lesions, skin lesions, ocular lesions and other types of biological samples as described herein—such as cerebrospinal fluid.

Compositions disclosed herein include amplification oligomers that can be used to specifically amplify selected nucleic acid sequences present in HSV genomic sequences, and nucleic acid probes for detecting the amplified sequences. Preferred embodiments include specific combinations of oligomers to amplify and detect HSV-1 and/or HSV-2 sequences in assays that provide a detectable signal or response within about 45 minutes from beginning of a transcription-associated amplification reaction.

The disclosed nucleic acid sequences and methods are useful for amplifying and detecting HSV nucleic acids from or derived from viral particles present in a sample in a relatively short time so that diagnosis can be made quickly and so effective treatment can be initiated and spread of the virus limited. The methods are useful for screening for individuals who have HSV infections but who do not exhibit definitive symptoms, or who have not seroconverted, and are particularly useful for screening patients who have a higher risk of death or serious complications from HSV infections, e.g., young, elderly, or immunocompromised individuals. The methods are also useful for rapid screening of many samples. The methods are useful because they minimize the risk of exposure of laboratory personnel to the infectious HSV agents, thereby limiting the risk of infection and spread of the virus. Thus, the methods and compositions disclosed herein respond to a need for rapid, sensitive, and specific testing of clinical samples that may contain HSV.

II. Definitions

To aid in understanding aspects of the disclosure, some terms used herein are described in more detail. All other scientific and technical terms used herein have the same meaning as commonly understood by those skilled in the relevant art, such as may be provided in *Dictionary ofMicrobiology and Molecular Biology,* 2nd ed. (Singleton et al., 1994, John Wiley & Sons, New York, N.Y.), *The Harper Collins Dictionary of Biology* (Hale & Marham, 1991, Harper Perennial, New York, N.Y.), and references cited herein. Unless mentioned otherwise, the techniques employed or contemplated herein are standard methods well-known to a person of ordinary skill in the art of molecular biology.

The terms "a," "an," and "the" include plural referents, unless the context clearly dictates otherwise. For example, "a nucleic acid," as used herein, is understood to represent one or more nucleic acids. As such, the terms "a" (or "an"), "one or more," and "at least one" can be used interchangeably herein.

A "sample" or "specimen," including "biological" or "clinical" samples may contain or may be suspected of containing HSV or components thereof, such as nucleic acids or fragments of nucleic acids. A sample may be a complex mixture of components. Samples include "biological samples" which include any tissue or material derived from a living or dead mammal or organism, including, e.g., blood, plasma, serum, blood cells, saliva, and mucous, cerebrospinal fluid (to diagnose HSV infections of the central nervous system) and samples—such as biopsies—from or derived from genital lesions, anogenital lesions, oral lesions, mucocutanoeus lesions, skin lesions and ocular lesions or combinations thereof. Samples may also include samples of in vitro cell culture constituents including, e.g., conditioned media resulting from the growth of cells and tissues in culture medium. The sample may be treated to physically or mechanically disrupt tissue or cell structure to release intracellular nucleic acids into a solution which may contain enzymes, buffers, salts, detergents and the like, to prepare the sample for analysis. In one step of the methods described herein, a sample is provided that is suspected of containing at least a HSV target nucleic acid. Accordingly, this step excludes the physical step of obtaining the sample from a subject.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see PCT No. WO 95/32305), phosphorothioate linkages, methylphosphonate linkages, or combinations thereof. Sugar moieties of the nucleic acid may be either ribose or deoxyribose, or similar compounds having known substitutions, e.g., 2' methoxy substitutions and 2' halide substitutions (e.g., 2'-F). Nitrogenous bases may be conventional bases (A, G, C, T, U), analogs thereof (e.g., inosine, 5-methylisocytosine, isoguanine; *The Biochemistry of the Nucleic Acids* 5-36, Adams et al., ed., 11$^{th}$ ed., 1992, Abraham et al., 2007, *BioTechniques* 43: 617-24), which include derivatives of purine or pyrimidine bases (e.g., N$^4$-methyl deoxyguanosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines, and pyrazolo-compounds, such as unsubstituted or 3-substituted pyrazolo[3,4-d]pyrimidine; U.S. Pat. Nos. 5,378,825, 6,949,367 and PCT No. WO 93/13121). Nucleic acids may include "abasic" residues in which the backbone does not include a nitrogenous base for one or more residues (U.S. Pat. No. 5,585,481). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., 2004, Biochemistry 43(42):13233-41). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well known in the art although nucleic acids may be purified from natural sources using routine techniques.

The term "polynucleotide" denotes a nucleic acid chain. Throughout this application, nucleic acids are designated by the 5'-terminus to the 3'-terminus. Standard nucleic acids, e.g., DNA and RNA, are typically synthesized "3'-to-5'," i.e., by the addition of nucleotides to the 5'-terminus of a growing nucleic acid.

A "nucleotide" is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O—Me, or 2' methoxy). As used herein, methoxy oligonucleotides containing "T" residues have a methoxy group at the 2' position of the ribose moiety, and a uracil at the base position of the nucleotide.

A "non-nucleotide unit" is a unit that does not significantly participate in hybridization of a polymer. Such units must not, for example, participate in any significant hydrogen bonding with a nucleotide, and would exclude units having as a component one of the five nucleotide bases or analogs thereof.

A "target nucleic acid" is a nucleic acid comprising a "target sequence" or "target region" to be amplified. Target nucleic acids may be DNA or RNA and may be either single-stranded or double-stranded. In a preferred embodiment of the invention, the target nucleic acid is RNA. In a more preferred embodiment, the target sequence is RNA encoded by at least a portion of either or both of the DNA sequences set forth in FIGS. 1A-C and 2A-B (SEQ ID NOs:1 and 2). The target nucleic acid may include other sequences besides the target sequence that may be amplified. In the instant disclosure, target nucleic acids are nucleic acids—such as DNA or RNA—from HSV, including HSV-1 and/or HSV-2. In a preferred embodiment, the target nucleic acid is RNA from HSV, including HSV-1 and/or HSV-2. In another preferred embodiment, the target nucleic acid comprises RNA encoded by the DNA sequence set forth in SEQ ID NOS: 1 (HSV-1) or SEQ ID NO: 2 (HSV-2). In another preferred embodiment, the target nucleic acid is RNA from HSV that has not been obtained by reverse transcription of HSV DNA. In other words, according to this embodiment, the target nucleic acid is RNA obtained directly from the virus or a cell infected with same.

In the context of nucleic acid amplification, the term "target sequence" is used interchangeably with the term "target region" to refer to the particular nucleotide sequence of the target nucleic acid that is to be amplified. The "target sequence" includes the complexing sequences to which oligonucleotides (e.g., priming oligonucleotides and/or promoter oligonucleotides) stably hybridize during an amplification process (e.g., PCR, TMA). In the specific context of oligonucleotide hybridization (e.g., hybridization of an amplification oligomer or detection probe to a segment of a target nucleic acid), the term "target sequence" refers to the sufficiently complementary region to which the oligonucleotide (or a portion thereof) stably hybridizes. Where the target nucleic acid is originally single-stranded, the term "target sequence" will also refer to the sequence complementary to the target sequence as present in the target nucleic acid. Where the target nucleic acid is originally double-stranded, the term "target sequence" refers to both the sense (+) and antisense (−) strands. In choosing a target sequence, the skilled artisan will understand that a sequence should be chosen so as to distinguish between unrelated or closely related target nucleic acids.

The terms "target(s) a sequence" or "target(s) a target nucleic acid" as used herein in reference to a region of HSV nucleic acid refers to a process whereby an oligonucleotide stably hybridizes to the target sequence in a manner that allows for amplification and/or detection as described herein. In one embodiment, the oligonucleotide is complementary to the targeted HSV nucleic acid sequence and contains no mismatches. In another embodiment, the oligonucleotide is complementary but contains 1; or 2; or 3; or 4; or 5 mismatches with the targeted HSV nucleic acid sequence. Preferably, the oligonucleotide that stably hybridizes to the HSV nucleic acid sequence includes at least 10, 11, 12, 13, 14, 15, 16, 17, 18, 19, 20, 21, 22, 23, 24, 25, 30, 35, 40, 45 or 50 nucleotides complementary to the target sequence. It is understood that at least 10 and as many as 50 is an inclusive range such that 10, 50 and each whole number there between are included. The term "configured to target a sequence" as used herein means that the target hybridizing region of an amplification oligonucleotide is designed to have a polynucleotide sequence that could target a sequence of the referenced HSV region, particularly, the referenced HSV-1 or HSV-2 region. Such an amplification oligonucleotide is not limited to targeting that sequence only, but is rather useful as a composition, in a kit or in a method for targeting a HSV target nucleic acid, as is described herein. The term "configured to" denotes an actual arrangement of the polynucleotide sequence configuration of the amplification oligonucleotide target hybridizing sequence.

Oligomer target-hybridizing sequences defined herein by reference to a specific sequence (e.g., by reference to a region within SEQ ID NO:1 or SEQ ID NO:2) are also understood to include functional complements thereof, unless the context clearly dictates otherwise. Thus, for example, where target-hybridizing regions of first and second amplification oligomers are defined by reference to specific sequences corresponding, respectively, to sense and antisense strands of a target nucleic acid, it is understood that the amplification oligomer combination may include a functional combination of first and second amplification oligomers having target-hybridizing sequences that are the respective complements of the specific reference sequences. Similarly, and again by way of example, where a target-hybridizing sequence for a detection probe oligomer is defined reference to a specific sequence, it is understood that the detection probe may include a corresponding detection probe oligomer having a target-hybridizing sequence that is the complement of the specific reference sequence; or where a detection probe oligomer is defined by its configuration to hybridize to a specific sequence, it is understood that the detection probe may include a corresponding detection probe oligomer having a target-hybridizing sequence that is configured to hybridize to the complement of the specific reference sequence. Oligomer sequences defined herein by reference to a specific sequence are also understood to include the DNA and RNA equivalents thereof (including DNA and RNA equivalents of functional complements thereof), unless the context clearly dictates otherwise.

The term "isolated," in reference to a nucleic acid, means that the nucleic acid is taken from its natural milieu, but the term does not connote any degree of purification.

The term "fragment," as used herein in reference to an HSV target nucleic acid, refers to a piece of contiguous nucleic acid, wherein the number of contiguous nucleotides in the fragment are less than that for the entire target nucleic acid.

The term "region" refers to a portion of a nucleic acid wherein the portion is smaller than the entire nucleic acid. For example, when the nucleic acid in reference is an oligonucleotide promoter provider, the term "region" may be used refer to the smaller promoter portion of the entire oligonucleotide. Similarly, and also as example only, when the nucleic acid is a target nucleic acid, the term "region" may be used to refer to a smaller area of the nucleic acid, wherein the smaller area is targeted by one or more oligonucleotides of the invention. For example, in reference to a target nucleic acid, "targets region" may be used to refer to a portion of the target nucleic acid to be amplified. As another non-limiting example, when the nucleic acid is in reference to an amplicon, the term "region" may be used to refer to the smaller nucleotide sequence identified for hybridization by the target-hybridizing sequence of a probe.

The interchangeable terms "oligomer," "oligo," and "oligonucleotide" refer to a nucleic acid having generally less than 1,000 nucleotide (nt) residues, including polymers in a range of from about 5 nt residues to about 900 nt residues, from about 10 nt residues to about 800 nt residues with a lower limit of about 12 to 15 nt and an upper limit of about 40 to 600 nt, and other embodiments are in a range having a lower limit of about 15 to 20 nt and an upper limit of about 22 to 100 nt. It is understood that these ranges are exemplary only, and an oligonucleotide may contain each whole number included in the range. Oligonucleotides may be purified from naturally occurring sources, but may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase, it may provide a promoter if it contains a sequence recognized by an RNA polymerase and allows for transcription (e.g., a T7 provider), and it may function to prevent hybridization or impede primer extension if appropriately situated and/or modified.

As used herein, an oligonucleotide having a nucleic acid sequence "comprising" or "consisting of" or "consisting essentially of" a sequence selected from a group of specific sequences means that the oligonucleotide, as a basic and novel characteristic, is capable of stably hybridizing to a nucleic acid having the exact complement of one of the listed nucleic acid sequences of the group under stringent hybridization conditions. An exact complement includes the corresponding DNA or RNA sequence.

As used herein, an oligonucleotide "substantially corresponding to" a specified nucleic acid sequence means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from a reference sequence and still hybridize to the same target nucleic acid sequence. It is also understood that a first nucleic acid corresponding to a second nucleic acid includes the RNA and DNA equivalents thereof and includes the complements thereof, unless the context clearly dictates otherwise. This variation from the nucleic acid may be stated in terms of a percentage of identical bases with the reference sequence or the percentage of perfectly complementary bases between the oligonucleotide and its target sequence. Thus, in certain embodiments, an oligonucleotide "substantially corresponds" to a reference nucleic acid sequence if these percentages of base identity or complementarity are from 100% to about 80%. In preferred embodiments, the percentage is from 100% to about 85%. In more preferred embodiments, this percentage is from 100% to about 90%; in other preferred embodiments, this percentage is at from 100% to about 95%, to about 96%, to about 97%, to about 98% or to about 99%. One skilled in the art will understand that the recited ranges include all whole and rational numbers of the range (e.g., 92% or 92.377%). One skilled in the art will further understand the various modifications to the hybridization conditions that might be required at various percentages of complementarity to allow hybridization to a specific target sequence without causing an unacceptable level of non-specific hybridization.

A "helper oligonucleotide" or "helper" refers to an oligonucleotide designed to bind to a target nucleic acid and impose a different secondary and/or tertiary structure on the target to increase the rate and extent of hybridization of a detection probe or other oligonucleotide with the targeted nucleic acid, as described, for example, in U.S. Pat. No. 5,030,557. Helpers may also be used to assist with the hybridization to target nucleic acid sequences and function of primer, target capture and other oligonucleotides. Helper oligonucleotides may be used in the methods described herein and may form part of the compositions and kits described herein.

As used herein, a "blocking moiety" is a substance used to "block" the 3'-terminus of an oligonucleotide or other nucleic acid so that it cannot be efficiently extended by a nucleic acid polymerase.

An "amplification oligomer", which may also be called an "amplification oligonucleotide," is an oligomer, at least the 3'-end of which is complementary to a target nucleic acid ("target hybridizing sequence"), and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is a "promoter-based amplification oligomer," which comprises a target hybridizing sequence and a promoter sequence for initiating transcription by an appropriate polymerase. Promoter-based amplification oligomers may or may not be extended by a polymerase in a primer-based extension depending upon whether or not the 3' end of the target hybridizing sequence is modified to prevent primer-based extension (e.g., a 3' blocked end). A promoter-based amplification oligonucleotide comprising a target hybridizing region that is not modified to prevent primer-based extension is referred to as a "promoter-primer." A promoter-based amplification oligonucleotide comprising a target hybridizing region that is modified to prevent primer-based extension is referred to as a "promoter-provider." Size ranges for amplification oligonucleotides include those comprising target hybridizing regions that are about 10 to about 70 nt long—such as about 10 to about 60 nt long, about 10 to about 50 nt long, about 10 to about 40 nt long, about 10 to about 30 nt long or about 10 to about 25 nt long or about 15 to 25 nt long. Preferred sizes of amplification oligomers include those comprising target hybridizing regions that are about 18, 19, 20, 21, 22 or 23 nt long. An amplification oligomer may optionally include modified nucleotides or analogs that are not complementary to target nucleic acid in a strict A:T/U, G:C sense. Such modified nucleotides or analogs are herein considered mismatched to their corresponding target sequence. For some embodiments, the preferred amount of amplification oligomer per reaction is about 10, 15 or 20 pmoles.

Oligomers not intended for primer-based extension by a nucleic acid polymerase may include a blocker group that replaces the 3'OH to prevent the enzyme-mediated extension of the oligomer in an amplification reaction. For example, blocked amplification oligomers and/or detection probes present during amplification may not have functional 3' OH and instead include one or more blocking groups located at or near the 3' end. In some embodiments, a blocking group near the 3' end is within five residues of the 3' end and is sufficiently large to limit binding of a polymerase to the oligomer. In other embodiments, a blocking group is covalently attached to the 3' terminus. Many different chemical groups may be used to block the 3' end, e.g., alkyl groups, non-nucleotide linkers, alkane-diol dideoxynucleotide residues, and cordycepin.

The term "promoter," as used herein, refers to a specific nucleic acid sequence that is recognized by a DNA-dependent RNA polymerase ("transcriptase") as a signal to bind to the nucleic acid and begin the transcription of RNA at a specific site.

As used herein, a "promoter-provider" or "provider" refers to an oligonucleotide comprising first and second regions, and which is modified to prevent the initiation of DNA synthesis from its 3'-terminus. The "first region" of a promoter-provider oligonucleotide comprises a base sequence which hybridizes to a DNA template, where the hybridizing sequence is situated 3', but not necessarily adjacent to, a promoter region. The target-hybridizing portion of a promoter oligonucleotide is typically at least 10, 11, 12, 13, 14, 15, 16, 17, 18, 19, 20, 21, 22, 23, 24, 25, 30, 35, 40 or 45 nucleotides in length, and may extend up to 50 or more nucleotides in length. The "second region" comprises a promoter sequence for an RNA polymerase. A promoter-provider oligonucleotide is configured so that it is incapable of being extended by an RNA- or DNA-dependent DNA polymerase, (e.g., reverse transcriptase), preferably by comprising a blocking moiety at its 3'-terminus as described above. This modification differentiates promoter providers from promoter primers. Preferably, the promoter portion of a promoter primer or provider is a promoter for a DNA-dependent RNA polymerase from *E. coli* and bacteriophages T7, T3, and SP6, though other promoters or modified version thereof can be used as well.

As used herein, a "terminating oligonucleotide" or "blocker oligonucleotide" is an oligonucleotide comprising a base sequence that is complementary to a region of the target nucleic acid in the vicinity of the 5'-end of the target sequence, so as to "terminate" primer extension of a nascent nucleic acid that includes a priming oligonucleotide, thereby providing a defined 3'-end for the nascent nucleic acid strand.

"Amplification" refers to any known procedure for obtaining multiple copies of a target nucleic acid sequence or its complement or fragments thereof. The multiple copies may be referred to as amplicons or amplification products. Known amplification methods include both thermal cycling and isothermal amplification methods. In some embodiments, isothermal amplification methods are preferred. Replicase-mediated amplification, polymerase chain reaction (PCR), ligase chain reaction (LCR), strand-displacement amplification (SDA), and transcription-mediated or transcription-associated amplification are non-limiting examples of nucleic acid amplification methods. Replicase-mediated amplification uses self-replicating RNA molecules, and a replicase such as QB-replicase (e.g., U.S. Pat.

No. 4,786,600). PCR amplification uses a DNA polymerase, pairs of primers, and thermal cycling to synthesize multiple copies of two complementary strands of dsDNA or from a cDNA (e.g., U.S. Pat. Nos. 4,683,195, 4,683,202, and 4,800,159). LCR amplification uses four or more different oligonucleotides to amplify a target and its complementary strand by using multiple cycles of hybridization, ligation, and denaturation (e.g., U.S. Pat. Nos. 5,427,930 and 5,516,663). SDA uses a primer that contains a recognition site for a restriction endonuclease and an endonuclease that nicks one strand of a hemimodified DNA duplex that includes the target sequence, whereby amplification occurs in a series of primer extension and strand displacement steps (e.g., U.S. Pat. Nos. 5,422,252; 5,547,861; and 5,648,211). Preferred embodiments use an amplification method suitable for the amplification of RNA target nucleic acids, such as transcription-mediated amplification (TMA) or NASBA, but it will be apparent to persons of ordinary skill in the art that oligomers disclosed herein may be readily used as primers in other amplification methods.

"Transcription-associated amplification," also referred to herein as "transcription-mediated amplification" (TMA), refers to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. TMA methods are embodiments of amplification methods used for amplifying and detecting HSV target sequences as described herein. Variations of transcription-associated amplification are well-known in the art as previously disclosed in detail (e.g., U.S. Pat. Nos. 4,868,105; 5,124,246; 5,130,238; 5,399,491; 5,437,990; 5,554,516; and 7,374,885; and PCT Pub. Nos. WO 88/01302, WO 88/10315, and WO 95/03430). The person of ordinary skill in the art will appreciate that the disclosed compositions may be used in amplification methods based on extension of oligomer sequences by a polymerase.

As used herein, the term "real-time TMA" refers to single-primer transcription-mediated amplification ("TMA") of target nucleic acid that is monitored by real-time detection means.

The term "amplicon," which is used interchangeably with "amplification product," refers to the nucleic acid molecule generated during an amplification procedure that is complementary or homologous to a sequence contained within the target sequence. These terms can be used to refer to a single strand amplification product, a double strand amplification product or one of the strands of a double strand amplification product. Double stranded amplicons can, in some aspects, be circularized using adapters. One such adapter is, for example, the SMRTBell (Pacific Biosciences, Menlo Park, Calif.). Circularized double stranded amplicons can be useful for many purposes, including, but not limited to, sequencing reactions.

"Probe," "detection probe," "detection oligonucleotide," and "detection probe oligomer" are used interchangeably herein to refer to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Probes may be DNA, RNA, analogs thereof or combinations thereof and they may be labeled or unlabeled. A probe's "target sequence" generally refers to a smaller nucleic acid sequence within a larger nucleic acid sequence that hybridizes specifically to at least a portion of a probe oligomer by standard base pairing. A probe may comprise target-specific sequences and other sequences that contribute to the three-dimensional conformation of the probe (e.g., U.S. Pat. Nos. 5,118,801; 5,312,728; 6,849,412; 6,835,542; 6,534,274; and 6,361,945; and US Pub. No. 20060068417). In a preferred embodiment, the detection probe comprises a 2' methoxy backbone which can result in a higher signal being obtained.

The term "TaqMan probe" refers to detection oligonucleotides that contain a fluorescent dye, typically on the 5' base, and a non-fluorescent quenching dye (quencher), typically on the 3' base. When irradiated, the excited fluorescent dye transfers energy to the nearby quenching dye molecule rather than fluorescing, resulting in a non-fluorescent substrate. During amplification, the exonuclease activity of the polymerase cleaves the TaqMan probe to separate the fluorophore from the quencher, thereby allowing an unquenched signal to be emitted from the fluorophore as an indicator of amplification.

By "stable" or "stable for detection" is meant that the temperature of a reaction mixture is at least 2° C. below the melting temperature of a nucleic acid duplex.

As used herein, a "label" refers to a moiety or compound joined directly or indirectly to a probe that is detected or leads to a detectable signal. Direct labelling can occur through bonds or interactions that link the label to the probe, including covalent bonds or non-covalent interactions, e.g., hydrogen bonds, hydrophobic and ionic interactions, or formation of chelates or coordination complexes. Indirect labelling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (e.g., U.S. Pat. Nos. 5,283,174, 5,656,207, and 5,658,737). Labels include chemiluminescent compounds, e.g., acridinium ester ("AE") compounds that include standard AE and derivatives (e.g., U.S. Pat. Nos. 5,656,207, 5,658,737, and 5,639,604). Synthesis and methods of attaching labels to nucleic acids and detecting labels are well known (e.g., Sambrook et al., Molecular Cloning, A Laboratory Manual, 2nd ed. (Cold Spring Harbor Laboratory Press, Cold Spring Harbor, N.Y., 1989), Chapter 10; U.S. Pat. Nos. 5,658,737, 5,656,207, 5,547,842, 5,283,174, and 4,581,333). More than one label, and more than one type of label, may be present on a particular probe, or detection may use a mixture of probes in which each probe is labeled with a compound that produces a detectable signal (e.g., U.S. Pat. Nos. 6,180,340 and 6,350,579).

As used herein, structures referred to as "molecular torches" are designed to include distinct regions of self-complementarity ("the closing domain") which are connected by a joining region ("the target binding domain") and which hybridize to one another under predetermined hybridization assay conditions. All or part of the nucleotide sequences comprising target closing domains may also function as target binding domains. Thus, target closing sequences can include, target binding sequences, non-target binding sequences, and combinations thereof.

"Capture probe," "capture oligonucleotide," "target capture oligonucleotide," and "capture probe oligomer" are used interchangeably herein to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes an oligonucleotide comprising two binding regions: a target hybridizing sequence and an immobilized probe-binding region. A variation of this example, the two regions may be present on two different oligomers joined together by one or more linkers. Another embodiment of a capture oligomer the target hybridizing sequence is a sequence that includes random or non-random poly-GU, poly-GT, or poly U sequences to bind non-specifically to a target nucleic acid and link it to an immobilized probe on a support (see, e.g., PCT Pub No. WO 2008/016988). The immobilized probe binding region can be a nucleic acid sequence, referred to as a tail. Tails include a substantially homopolymeric tail of about 10 to 40 nucleotides (e.g., $A_{10}$ to $A_{40}$), or of about 14 to 33 nt (e.g., $T_3A_{14}$ to $T_3A_{30}$), that bind to a complementary immobilized sequence attached to the support particle or support matrix. Thus, a non-limiting example of preferred nucleic acid tails can in some embodiments include $T_{0-4}A_{10-40}$ sequences. Another example of a capture oligomer comprises two regions, a target hybridizing sequence and a binding pair member that is not a nucleic acid sequence.

As used herein, an "immobilized oligonucleotide," "immobilized probe" or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size ±5%), to which an immobilized probe is joined directly (via covalent linkage, chelation, or ionic interaction), or indirectly (via one or more linkers), where the linkage or interaction between the probe and support is stable during hybridization conditions.

By "complementary" is meant that the nucleotide sequences of similar regions of two single-stranded nucleic acids, or to different regions of the same single-stranded nucleic acid have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g., G:C, A:T or A:U pairing). By "sufficiently complementary" is meant a contiguous sequence that is capable of hybridizing to another sequence by hydrogen bonding between a series of complementary bases, which may be complementary at each position in the sequence by standard base pairing or may contain one or more residues that are not complementary by standard A:T/U and G:C pairing or are modified nucleotides such as abasic residues, modified nucleotides or nucleotide analogs. Sufficiently complementary contiguous sequences typically are at least 80%, or at least 90%, complementary to a sequence to which an oligomer is intended to specifically hybridize (a %-complementarity range includes all whole and rational numbers of the range). Sequences that are "sufficiently complementary" allow stable hybridization of a nucleic acid oligomer with its target sequence under appropriate hybridization conditions, even if the sequences are not completely complementary. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "completely" complementary (see, e.g., Sambrook et al., *Molecular Cloning, A Laboratory Manual*, $2^{nd}$ ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57).

By "preferentially hybridize" or "specifically hybridize" is meant that under stringent hybridization assay conditions, an oligonucleotide hybridizes to its target sequences, or replicates thereof, to form stable oligonucleotide: target sequence hybrid, while at the same time formation of stable oligonucleotide: non-target sequence hybrid is minimized. For example, a probe oligonucleotide preferentially hybridizes to a target sequence or replicate thereof to a sufficiently greater extent than to a non-target sequence, to enable one having ordinary skill in the art to accurately detect the RNA replicates or complementary DNA (cDNA) of the target sequence formed during the amplification. Appropriate hybridization conditions are well known in the art for probe, amplification, target capture, blocker and other oligonucleotides, may be predicted based on sequence composition, or can be determined by using routine testing methods (see, e.g., Sambrook et al., *Molecular Cloning, A Laboratory Manual*, $2^{nd}$ ed. (Cold Spring Harbor Laboratory Press, Cold Spring Harbor, NY, 1989) at §§ 1.90-1.91, 7.37-7.57, 9.47-9.51 and 11.47-11.57, particularly §§ 9.50-9.51, 11.12-11.13, 11.45-11.47 and 11.55-11.57).

By "nucleic acid hybrid," "hybrid," or "duplex" is meant a nucleic acid structure containing a double-stranded, hydrogen-bonded region wherein each strand is complementary to the other, and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

"Sample preparation" refers to any steps or methods that treat a sample for subsequent amplification and/or detection of HSV nucleic acids present in the sample. The target nucleic acid may be a minority component in the sample. Sample preparation may include any known method of isolating or concentrating components, such as viruses or nucleic acids using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically captures a target nucleic acid and separates it from other sample components (e.g., as described in U.S. Pat. No. 6,110,678 and PCT Pub. No. WO 2008/016988).

"Separating" or "purifying" means that one or more components of a sample are removed or separated from other sample components. Sample components include target nucleic acids usually in a generally aqueous solution phase, which may also include cellular fragments, proteins, carbohydrates, lipids, and other nucleic acids. Separating or purifying removes at least 70%, or at least 80%, or at least 95% of the target nucleic acid from other sample components. Ranges of %-purity include all whole and rational numbers of the range.

As used herein, a "DNA-dependent DNA polymerase" is an enzyme that synthesizes a complementary DNA copy from a DNA template. Examples are DNA polymerase I from E. coli, bacteriophage T7 DNA polymerase, or DNA polymerases from bacteriophages T4, Phi-29, M2, or T5. DNA-dependent DNA polymerases may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases typically also have DNA-dependent DNA polymerase activity.

As used herein, a "DNA-dependent RNA polymerase" or "transcriptase" is an enzyme that synthesizes multiple RNA copies from a double-stranded or partially double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from E. coli and bacteriophages T7, T3, and SP6.

As used herein, an "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. RTs may also have an RNAse H activity. A primer is required to initiate synthesis with both RNA and DNA templates.

As used herein, a "selective RNAse" is an enzyme that degrades the RNA portion of an RNA:DNA duplex but not single-stranded RNA, double-stranded RNA or DNA. An exemplary selective RNAse is RNAse H. Enzymes possessing the same or similar activity as RNAse H may also be used. Selective RNAses may be endonucleases or exonucleases. Most reverse transcriptase enzymes contain an RNAse H activity in addition to their polymerase activities. However, other sources of the RNAse H are available without an associated polymerase activity. The degradation may result in separation of RNA from a RNA:DNA complex. Alternatively, a selective RNAse may simply cut the RNA at various locations such that portions of the RNA melt off or permit enzymes to unwind portions of the RNA. Other enzymes that selectively degrade RNA target sequences or RNA products of the present invention will be readily apparent to those of ordinary skill in the art.

The term "specificity," in the context of an amplification system, is used herein to refer to the characteristic of an amplification system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio).

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

As used herein, the term "relative fluorescence unit" ("RFU") is an arbitrary unit of measurement of fluorescence intensity. RFU varies with the characteristics of the detection means used for the measurement.

III. Oligonucleotides for Amplification and Detection of HSV

Compositions disclosed herein include, e.g., amplification oligomers that can be used to specifically amplify selected HSV-1 or HSV-2 nucleic acid sequences, and optionally nucleic acid probes for detecting the amplified sequences.

Oligonucleotides for amplifying an HSV-1 or HSV-2 target nucleic acid typically comprise at least two amplification oligomers. Some embodiments of the invention may utilize three, four, five, six, seven, or even eight or more amplification oligomers in, for example, multiplex amplification assays. Thus, by way of example, oligonucleotides for amplifying an HSV-1 and/or HSV-2 target nucleic acid may comprise one, two, three, four, or five or more forward amplification primers and one, two, three, four, or five or more reverse amplification primers. In one embodiment, at least two amplification oligomers are used in order to generate an amplicon that can be subsequently detected, where the at least two amplification oligomers are configured to specifically hybridize to a region within a target nucleic acid selected from (a) a target nucleic corresponding to the HSV-1 UL42 gene and (b) a target nucleic acid corresponding to the HSV-2 UL42 gene. Suitably, the amplicon is detectable using a detection probe. Typically, the amplicon is from about 50 to about 200 nucleotides in length (e.g., about 80 to about 140 nucleotides in length or about 90 to about 115 nucleotides in length), including all whole numbers between 50 and 200 that are not explicitly listed here. In particular variations, at least two amplification oligomers for amplifying an HSV-1 target nucleic acid region are configured to specifically hybridize to a region corresponding to nucleotides 602-709 or 617-709 of SEQ ID NO:1; and/or at least two amplification oligomers for amplifying an HSV-2 target nucleic acid region are configured to specifically hybridize to a region corresponding to nucleotides 524-605, 581-654, or 524-654 of SEQ ID NO:2. In certain embodiments, a combination of oligonucleotides includes amplification oligomers selected from oligomers described herein for amplifying both an HSV-1 target nucleic acid and an HSV-2 target nucleic acid.

In particular embodiments of the present invention, at least two amplification oligomers for amplifying an HSV-1 or HSV-2 target nucleic acid comprise (i) a first amplification oligomer that includes a target-hybridizing sequence substantially corresponding to, comprising, consisting of, or consisting essentially of a target-specific oligomer sequence as shown in Table 17, infra (or substantially corresponding to, comprising, consisting of, or consisting essentially of a sequence contained in an oligomer region and including a core oligomer sequence as shown in Table 17), and (ii) a second amplification oligomer that includes a target-hybridizing sequence substantially corresponding to, comprising, consisting of, or consisting essentially of a target-specific oligomer sequence as shown in Table 17 (or substantially corresponding to, comprising, consisting of, or consisting essentially of a sequence contained in an oligomer region and including a core oligomer sequence as shown in Table 17), where the first and second amplification oligomers correspond to the same target nucleic acid, and where the target-hybridizing sequences are selected such that, for any oligomer pair, an antisense sequence is situated downstream of a sense sequence (i.e., the first and second amplification oligomers are situated such that they flank a target region to be amplified). In specific variations, the first and/or second amplification oligomer—or the first and/or second target-hybridizing sequence of a first and/or second amplification oligomer—comprises or consists of an oligomer sequence selected from the amplification oligonucleotide sequences shown in Table 17. The probe target-hybridizing sequences disclosed in Table 17 may be used as amplification oligomer target-hybridization regions; likewise, amplification oligomer target-hybridizing sequences disclosed in Table 17 may be used as probe target-hybridizing sequences. Although the oligomer sequences in Table 17 are shown as either DNA or RNA, equivalent RNA or DNA sequences, respectively, can be readily derived by the person skilled in the art and are to be considered as falling within the definition of "oligomer." In addition, complementary sequences of DNA and RNA and reverse complementary sequences can be readily derived by the skilled person. It is therefore to be understood that a description of any individual sequence of DNA, for example, encompasses its complement, its reverse complement, and equivalent RNA sequences.

In certain aspects of the invention, a combination of at least two oligomers is provided for determining the presence or absence of Herpes Simplex Virus 1 (HSV-1) in a sample. Typically, the oligomer combination includes first and second amplification oligomers for amplifying a target region of an HSV-1 target nucleic acid corresponding to a region of the nucleotide sequence shown in SEQ ID NO:1. For example, in some embodiments, the first amplification oligomer comprises a first target-hybridizing sequence that is from about 15 to about 27 contiguous nucleotides in length and substantially corresponding to, or identical to, a sequence that is contained in the sequence of SEQ ID NO:31 and/or includes at least the sequence of SEQ ID NO:30; and/or the second amplification oligomer comprises a second target-hybridizing sequence that is from about 15 to about 27 contiguous nucleotides in length and substantially corresponding to, or identical to, a sequence that is contained in the sequence of SEQ ID NO:33 and/or includes at least the sequence of SEQ ID NO:32. Typically, the first target-hybridizing sequence substantially corresponds to, or is identical to, a sequence that is contained in the sequence of SEQ ID NO:31 and includes at least the sequence of SEQ ID NO:30; and the second target-hybridizing sequence substantially corresponds to, or is identical to, a sequence that is contained in the sequence of SEQ ID NO:33 and includes at least the sequence of SEQ ID NO:32.

In some embodiments of the oligomer combination for determining the presence or absence of HSV-1, the first target-hybridizing sequence substantially corresponds to, or is identical to, a sequence that is contained in the sequence of SEQ ID NO:29 and/or includes at least the sequence of SEQ ID NO:28. In typical variations, the first target-hybridizing sequence substantially corresponds to, or is identical to, a sequence that is contained in the sequence of SEQ ID NO:29 and includes at least the sequence of SEQ ID NO:28. In specific variations, the first target-hybridizing sequence substantially corresponds to, or is identical to, the sequence shown in SEQ ID NO:20, SEQ ID NO:6, or SEQ ID NO:12. In certain embodiments, the second target-hybridizing sequence substantially corresponds to, or is identical to, the sequence shown in SEQ ID NO:7 or SEQ ID NO:9.

In more particular variations of an oligomer combination as above, the first and second target-hybridizing sequences substantially correspond to, or are identical to, the sequences shown in (i) SEQ ID NO:20 and SEQ ID NO:7, respectively (ii) SEQ ID NO:6 and SEQ ID NO:7, respectively, or (iii) SEQ ID NO:6 and SEQ ID NO:9, respectively.

In certain embodiments, an amplification oligomer for determining the presence or absence of HSV-1 is a promoter primer or promoter provider further comprising a promoter sequence located 5' to the target-hybridizing sequence and which is not non-complementary to the HSV-1 target nucleic acid. For example, in some embodiments of an oligomer combination as described herein for amplification of an HSV-1 UL42 target region, the first amplification oligomer is a promoter primer or promoter provider further comprising a 5' promoter sequence. In particular embodiments, the promoter sequence is a T7 RNA polymerase promoter sequence such as, for example, a T7 promoter sequence having the nucleotide sequence shown in SEQ ID NO:54. In specific variations, the first amplification oligomer is a promoter primer or promoter provider having the sequence shown in SEQ ID NO:19, SEQ ID NO:5, or SEQ ID NO:11.

In some embodiments, an oligomer combination for determining the presence or absence of HSV-1 as above further includes at least one detection probe oligomer configured to specifically hybridize to an HSV-1 target sequence that is amplifiable using the first and second amplification oligomers (e.g., an HSV-1 target sequence that is flanked by the target-hybridizing sequences of the first and second amplification oligomers). In typical variations, a detection probe oligomer for use in accordance with the present invention includes a target-hybridizing sequence that is from about 14 to about 40 nucleotides in length and is configured to specifically hybridize to a target sequence contained within SEQ ID NO:1 from about nucleotide position 635 to about nucleotide position 683. For example, in some variations, the detection probe target-hybridizing sequence substantially corresponds to, or is identical to, a sequence that is contained in the sequence of SEQ ID NO:40 or SEQ ID NO:41 and/or includes at least the sequence of SEQ ID NO:34, SEQ ID NO:35, or SEQ ID NO:38; in some such embodiments, the detection probe target-hybridizing sequence substantially corresponds to, or is identical to, a sequence that is contained in the sequence of SEQ ID NO:40 or SEQ ID NO:41 and includes at least the sequence of SEQ ID NO:34, SEQ ID NO:35, or SEQ ID NO:38.

In some embodiments, a detection probe target-hybridizing sequence as above substantially corresponds to, or is identical to, a sequence that includes at least the sequence of SEQ ID NO:34 or SEQ ID NO:35 and that is contained in the sequence of SEQ ID NO:36 or SEQ ID NO:37. Particularly suitable detection probe target-hybridizing sequences substantially correspond to, or are identical to, the sequence shown in SEQ ID NO:8 or SEQ ID NO:22; in some such variations, the first and second amplification oligomer target-hybridizing sequences substantially correspond to, or are identical to, the sequences shown in (i) SEQ ID NO:20 and SEQ ID NO:7, respectively (ii) SEQ ID NO:6 and SEQ ID NO:7, respectively, or (iii) SEQ ID NO:6 and SEQ ID NO:9, respectively.

In other embodiments, an HSV-1 detection probe target-hybridizing sequence substantially corresponds to, or is identical to, a sequence that includes at least the sequence of SEQ ID NO:38 and that is contained in the sequence of SEQ ID NO:39. In specific variations, the detection probe target-hybridizing sequence substantially corresponds to, or is identical to, the sequence shown in SEQ ID NO:10; in some such variations, the first and second amplification oligomer target-hybridizing sequences substantially correspond to, or are identical to, the sequences shown in (i) SEQ ID NO:20 and SEQ ID NO:7, (ii) SEQ ID NO:6 and SEQ ID NO:7, or (iii) SEQ ID NO:6 and SEQ ID NO:9.

In other aspects of the invention, a combination of at least two oligomers is provided for determining the presence or absence of Herpes Simplex Virus 2 (HSV-2) in a sample. Typically, the oligomer combination includes first and second amplification oligomers for amplifying a target region of an HSV-2 target nucleic acid corresponding to a region of the nucleotide sequence shown in SEQ ID NO:2. For example, in some embodiments, the first amplification oligomer comprises a first target-hybridizing sequence that is from about 15 to about 27 contiguous nucleotides in length and substantially corresponding to, or identical to, a sequence that (i) is contained in the sequence of SEQ ID NO:49 and/or includes at least the sequence of SEQ ID NO:48 or (ii) is contained in the sequence of SEQ ID NO:43 and/or includes at least the sequence of SEQ ID NO:42; and the second amplification oligomer comprises a second target-hybridizing sequence that is from about 15 to about 27 contiguous nucleotides in length and substantially corresponding to a sequence that (i) is contained in the sequence of SEQ ID NO:51 and/or includes at least the sequence of SEQ ID NO:50 or (ii) is contained in the sequence of SEQ ID NO:45 and/or includes at least the sequence of SEQ ID NO:44.

In some embodiments of the oligomer combination for determining the presence or absence of HSV-2 is a sample, the first target hybridizing sequence substantially corresponds to, or is identical to, a sequence that is contained in the sequence of SEQ ID NO:49 and/or includes at least the sequence of SEQ ID NO:48; and/or the second target hybridizing sequence substantially corresponds to, or is identical to, a sequence that is contained in the sequence of SEQ ID NO:51 and/or includes at least the sequence of SEQ ID NO:50. In typical variations, the first target hybridizing sequence substantially corresponds to, or is identical to, a sequence that is contained in the sequence of SEQ ID NO:49 and includes at least the sequence of SEQ ID NO:48; and the second target hybridizing sequence substantially corresponds to, or is identical to, a sequence that is contained in the sequence of SEQ ID NO:51 and includes at least the sequence of SEQ ID NO:50. In particular variations, the first target-hybridizing sequence substantially corresponds to, or is identical to, the sequence shown in SEQ ID NO:24 and/or the second target hybridizing sequence substantially corresponds to, or is identical to, the sequence shown in SEQ ID NO:25.

In other embodiments of the oligomer combination for determining the presence or absence of HSV-2 is a sample, the first target hybridizing sequence substantially corresponds to, or is identical to, a sequence that is contained in the sequence of SEQ ID NO:43 and/or includes at least the sequence of SEQ ID NO:42; and/or the second target hybridizing sequence substantially corresponds to, or is identical to, a sequence that is contained in the sequence of SEQ ID NO:45 and/or includes at least the sequence of SEQ ID NO:44. In typical variations, the first target hybridizing sequence substantially corresponds to, or is identical to, a sequence that is contained in the sequence of SEQ ID NO:43 and includes at least the sequence of SEQ ID NO:42; and the second target hybridizing sequence substantially corresponds to, or is identical to, a sequence that is contained in the sequence of SEQ ID NO:45 and includes at least the sequence of SEQ ID NO:44. In particular variations, the first target-hybridizing sequence substantially corresponds to, or is identical to, the sequence shown in SEQ ID NO:14 and/or the second target-hybridizing sequence substantially corresponds to, or is identical to, the sequence shown in SEQ ID NO:15.

In some embodiments, an amplification oligomer for determing the presence or absence of HSV-2 is a promoter primer or promoter provider further comprising a promoter sequence located 5' to the target-hybridizing sequence and which is not non-complementary to the HSV-2 target nucleic acid. For example, in some embodiments of an oligomer combination as described herein for amplification of an HSV-2 UL42 target region, the first amplification oligomer is a promoter primer or promoter provider further comprising a 5' promoter sequence. In particular embodiments, the promoter sequence is a T7 RNA polymerase promoter sequence such as, for example, a T7 promoter sequence having the nucleotide sequence shown in SEQ ID NO:54. In specific variations, the first amplification oligomer is a promoter primer or promoter provider having the sequence shown in SEQ ID NO:23 or SEQ ID NO:13.

In some embodiments, an oligomer combination for determining the presence or absence of HSV-1 as above further includes at least one detection probe oligomer configured to specifically hybridize to an HSV-2 target sequence that is amplifiable using the first and second amplification oligomers (e.g., an HSV-2 target sequence that is flanked by the target-hybridizing sequences of the first and second amplification oligomers). In certain variations—e.g., where the first target hybridizing sequence substantially corresponds to, or is identical to, a sequence that is contained in the sequence of SEQ ID NO:49 and includes at least the sequence of SEQ ID NO:48, and the second target hybridizing sequence substantially corresponds to, or is identical to, a sequence that is contained in the sequence of SEQ ID NO:51 and includes at least the sequence of SEQ ID NO:50—a detection probe oligomer for use in accordance with the present invention includes a target-hybridizing sequence that is from about 14 to about 25 nucleotides in length and configured to specifically hybridize to a target sequence contained within SEQ ID NO:2 from about nucleotide position 608 to about nucleotide position 632. In certain variations, the detection probe target-hybridizing sequence substantially corresponds to, or is identical to, a sequence that is contained in the sequence of SEQ ID NO:53 and includes at least the sequence of SEQ ID NO:52. Particularly suitable detection probe target-hybridizing sequences substantially correspond to, or are identical to, the sequence shown in SEQ ID NO:27; in some such variations, the first and second amplification oligomer target-hybridizing sequences substantially correspond to, or are identical to, the sequences shown in SEQ ID NO:24 and SEQ ID NO:25, respectively.

In other embodiments of an oligomer combination for determining the presence or absence of HSV-2 comprising a detection probe—e.g., where the first target hybridizing sequence substantially corresponds to, or is identical to, a sequence that is contained in the sequence of SEQ ID NO:43 and includes at least the sequence of SEQ ID NO:42, and the second target hybridizing sequence substantially corresponds to, or is identical to, a sequence that is contained in the sequence of SEQ ID NO:45 and includes at least the sequence of SEQ ID NO:44—the detection probe oligomer includes a target-hybridizing sequence that is from about 14 to about 30 nucleotides in length and configured to specifically hybridize to a target sequence contained within SEQ ID NO:2 from about nucleotide position 549 to about nucleotide position 578. In certain variations, the detection probe target-hybridizing sequence substantially corresponds to, or is identical to, a sequence that is contained in the sequence of SEQ ID NO:47 and includes at least the sequence of SEQ ID NO:46. Particularly suitable detection probe target-hybridizing sequences substantially correspond to, or are identical to, the sequence shown in SEQ ID NO:16; in some such variations, the first and second amplification oligomer target-hybridizing sequences substantially correspond to, or are identical to, the sequences shown in SEQ ID NO:14 and SEQ ID NO:15, respectively.

Typically, a detection probe oligomer in accordance with the present invention further includes a label. Particularly suitable labels include compounds that emit a detectable light signal, e.g., fluorophores or luminescent (e.g., chemiluminescent) compounds that can be detected in a homogeneous mixture. More than one label, and more than one type of label, may be present on a particular probe, or detection may rely on using a mixture of probes in which each probe is labeled with a compound that produces a detectable signal (see, e.g., U.S. Pat. Nos. 6,180,340 and 6,350,579). Labels may be attached to a probe by various means including covalent linkages, chelation, and ionic interactions, but preferably the label is covalently attached. For example, in some embodiments, a detection probe has an attached chemiluminescent label such as, e.g., an acridinium ester (AE) compound (see, e.g., U.S. Pat. Nos. 5,185,439; 5,639, 604; 5,585,481; and 5,656,744), which in typical variations is attached to the probe by a non-nucleotide linker (see, e.g., U.S. Pat. Nos. 5,585,481; 5,656,744; and 5,639,604, particularly at column 10, line 6 to column 11, line 3, and Example 8; each incorporated by reference herein). In other embodiments, a detection probe comprises both a fluorescent label and a quencher, a combination that is particularly useful in fluorescence resonance energy transfer (FRET) assays. Specific variations of such detection probes include, e.g., a TaqMan® detection probe (Roche Molecular Diagnostics) and a "molecular beacon" (see, e.g., Tyagi et al., *Nature Biotechnol.* 16:49-53, 1998; U.S. Pat. Nos. 5,118,801 and 5,312,728).

A detection probe oligomer in accordance with the present invention may further include a non-target-hybridizing sequence. Specific embodiments of such detection probes include, for example, probes that form conformations held by intramolecular hybridization, such as conformations generally referred to as hairpins. Particularly suitable hairpin probes include a "molecular torch" (see, e.g., U.S. Pat. Nos. 6,849,412; 6,835,542; 6,534,274; and 6,361,945) and a "molecular beacon" (see, e.g., Tyagi et al., supra; U.S. Pat. Nos. 5,118,801 and 5,312,728, supra). Methods for using such hairpin probes are well-known in the art.

In yet other embodiments, a detection probe is a linear oligomer that does not substantially form a conformation held by intramolecular bonds. In specific variations, a linear detection probe oligomer includes a chemiluminescent compound as the label, preferably an acridinium ester (AE) compound.

An oligomer combination for determining the presence or absence of HSV-1 or HSV-2 as above may also include at least one capture probe oligomer. The capture probe oligomer typically comprises a target-hybridizing sequence substantially corresponding to a sequence contained in the complement of SEQ ID NO:1 or SEQ ID NO:2. In some such embodiments, the capture probe target-hybridizing sequence is covalently attached to a sequence or moiety that binds to an immobilized probe. Suitable target-hybridizing sequences substantially correspond to, or are identical to, the sequence shown in SEQ ID NO:4, SEQ ID NO:18, SEQ ID NO:70, or SEQ ID NO:72. In more particular variations, the capture probe oligomer has a sequence selected from SEQ ID NO:3, SEQ ID NO:17, SEQ ID NO:69, and SEQ ID NO:71.

In certain embodiments of an oligomer combination that includes at least one capture probe oliogmer, the capture probe oligomer comprises a target-hybridizing sequence substantially corresponding to, or identical to, a sequence that is from about 15 to about 30 contiguous nucleotides contained in the sequence of SEQ ID NO:76 and includes at least the sequence of SEQ ID NO:75. In some variations, the capture probe target-hybridizing sequence substantially corresponds to, or is identical to, a sequence that is contained in the sequence of SEQ ID NO:74 and/or includes at least the sequence of SEQ ID NO:75. For example, the target-hybridizing sequence may substantially correspond to, or be identical to, the sequence shown in SEQ ID NO:70 or SEQ ID NO:72. Typically, the capture probe target-hybridizing sequence is covalently attached to a sequence or moiety that binds to an immobilized probe. In some embodiments, the oligomer combination further includes a second capture probe oligomer comprising a target-hybridizing sequence (typically covalently attached to a sequence or moiety that binds to an immobilized probe) configured to specifically hybridize to the HSV-1 and/or HSV-2 target nucleic acid. In some such variations, the second capture probe oligomer has a target-hybridizing sequence substantially corresponding to, or identical to, the sequence shown in SEQ ID NO:4 or SEQ ID NO:18. In particular variations, the first capture probe oligomer has the sequence shown in SEQ ID NO:69 or SEQ ID NO:71 and the second capture probe oligomer has the sequence shown in SEQ ID NO:3 or SEQ ID NO:17.

Oligonucleotides for amplifying and detecting an HSV target are also shown in Table 17. Their preferred function is included for each sequence, and for sequences identified as promoter primers as the preferred function, the sequences include a 5' T7 bacteriophage promoter sequence from which a T7 RNA polymerase can initiate transcription under appropriate conditions. Those skilled in the art will appreciate that another 5' promoter sequence may be substituted for the T7 promoter sequence, which would then function with the appropriate RNA polymerase for the chosen other promoter sequence, to make an equivalent promoter primer oligonucleotide. Oligomers having the same target-specific sequences as the promoter primers but without the promoter sequence are also shown (referred to as a "target hybridizing sequence" of the respective promoter primer) and are capable of functioning as primers in amplification systems that do not use promoter primers. Those skilled in the art will recognize that oligomers identified as having a preferred function in target capture have target-specific portions and optionally include tail portions (e.g. $T_3A_{30}$) which may be deleted or substituted with other sequences or binding moieties.

Embodiments of oligomers may include one or more modified residues affecting the backbone structure (e.g., 2'-methoxy substituted RNA groups), or one or more LNA monomers, preferably at 5' residues of a primer oligomer, or may include a non-nucleotide linker to attach a label to the oligomer. In a preferred embodiment, oligomers that function as probes for RNA targets may be synthesized with 2'-methoxy substituted RNA groups to promote more stable hybridization between probe and target sequences.

Preferred embodiments of target capture oligomers include a target-specific sequence that binds specifically to the HSV target nucleic acid and a covalently linked "tail" sequence (e.g., $T_{0-4}A_{10-36}$) used in capturing the hybridization complex containing the target nucleic acid to an immobilized sequence on a solid support. Capture oligomers may include at least one 2' methoxy linkage. Embodiments of capture oligomers may include the target-specific sequence that binds to HSV nucleic acid attached to another binding moiety, e.g., a biotinylated sequence that binds specifically to immobilized avidin or streptavidin. The tail sequence or binding moiety binds to an immobilized probe (e.g., complementary sequence or avidin) to capture the hybridized target and separate it from other sample components by separating the solid support from the mixture.

Amplification oligomer sequences, including promoter primer sequences, bind specifically to the target nucleic acid or its complementary sequence and may contain additional sequences that are not target-specific, e.g., the promoter sequence in a promoter primer. A target-specific sequence, with or without an attached promoter sequence, may serve as an amplification oligomer in a variety of in vitro amplification processes. Embodiments of the HSV assays may use amplification methods that require multiple cycling reaction temperatures, such as PCR (U.S. Pat. Nos. 4,683,195, 4,683, 202, and 4,800,159), or may be substantially isothermal as in, for example, transcription associated amplification methods, such as TMA or NASBA (e.g., U.S. Pat. Nos. 5,399, 491, 5,480,784, 5,824,518, 5,888,779, 5,786,183, 5,437,990, 5,130,238, 4,868,105, and 5,124,246, and PCT Nos. WO 8801302 and WO 8810315). The HSV assays may use amplification systems that are detected during the amplification process (e.g., real time detection) by including probes that emit distinguishable fluorescent signals when the probe is bound to the intended target sequence made during the amplification process. Probes for real time detection include those referred to as "molecular beacon" or "molecular switch" probes (e.g., U.S. Pat. Nos. 5,118,801 and 5,312, 728, Lizardi et al., U.S. Pat. Nos. 5,925,517 and 6,150,097, Tyagi et al., Giesendorf et al., 1998, Clin. Chem. 44(3):482-6) and "molecular torch" probes (e.g., U.S. Pat. Nos. 6,835, 542 and 6,849,412, Becker et al.). Generally, such probes include a reporter dye attached to one end of the probe oligomer (e.g., FAM™, TET™, JOE™, VIC™) and a quencher compound (e.g., TAMRA™ or non-fluorescent quencher) attached to the other end of the probe oligomer, and signal production depends on whether the two ends with their attached compounds are in close proximity or separated.

Also provided by the present invention are detection probe oligomers and capture probe oligomers as described herein.

IV. Methods for Amplification and Detection of HSV

In other aspects, the present invention provides methods for detecting an HSV-1 and/or HSV-2 target nucleic acid in a sample using an oligomer combination as described herein. Such a method generally includes (1) contacting the sample, suspected of containing HSV-1 or HSV-2, with at least two oligomers for amplifying a target region of an HSV-1 or HSV-2 target nucleic acid, where the at least two oligomers include first and second amplification oligomers as described above; (2) performing an in vitro nucleic acid amplification reaction (e.g., a transcription-associated amplification reaction), where any HSV-1 or HSV-2 target nucleic acid present in the sample is used as a template for generating an amplification product; and (3) detecting the presence or absence of the amplification product, thereby indicating the presence or absence of HSV-1 or HSV-2 in the sample. A detection method in accordance with the present invention typically further includes the step of obtaining the sample to be contacted with the at least two oligomers. In certain embodiments, "obtaining" a sample to be used in steps (1)-(3) includes, for example, receiving the sample from a testing facility or other location where one or more steps of the method are performed, and/or retrieving the sample from a location (e.g., from storage or other depository) within a facility where one or more steps of the method are performed. Detecting the amplified nucleic acid may be performed by hybridizing the amplification product to a probe sequence such as, for example, a detection probe as described above. Detection may be at the end of the amplification reaction or may be performed in real-time. For detection, the amplified nucleic acid may be labeled and bound to an unlabeled probe, but preferred embodiments bind a labeled probe to the amplified nucleic acid. For real-time detection, a labeled probe may be used that is detected in a homogeneous system. In certain variations, the method is for determining the presence or absence of both the HSV-1 and HSV-2 target nucleic acids such as, for example, in a multiplex assay.

For embodiments utilizing a detection probe, the probe preferably is labeled and produces a signal detected in a homogeneous system, i.e., without separation of bound probe from unbound probe. In some variations, probes are labeled with an acridinium ester (AE) compound from which a chemiluminescent signal is produced and detected in a homogeneous system (substantially as described in detail in U.S. Pat. Nos. 5,283,174, 5,656,744, and 5,658, 737). Other examples of probes may be labeled with a fluorescent compound which emits a detectable signal only when the probe is bound to its target, e.g., molecular switch, molecular beacon, or molecular torch probes.

In one embodiment, probes for the specific detection of HSV-1 sequences are labeled differently to probes for the specific detection of HSV-2 sequences. Thus, the signal that is obtained from the labeled probe will be indicative of the presence of HSV-1 or HSV-2 or a combination thereof in the sample, Assays for detection of HSV nucleic acid may include an internal control (IC) nucleic acid that is amplified and detected by using IC-specific primers and probe in the same reaction mixtures used for HSV nucleic acid amplification and detection. Amplification and detection of the IC-specific sequence demonstrates that assay reagents and conditions were properly used even when no HSV-specific signal is detected for a tested sample (i.e., negative samples). The IC may be used as an internal calibrator for the assay that provides a quantitative result. The IC may be a randomized sequence derived from a naturally occurring source that is not HSV.

Sample Preparation

Preparation of samples for amplification and detection of HSV sequences may include methods of separating and/or concentrating viruses contained in a sample from other sample components. Sample preparation may include routine methods of disrupting samples or lysing samples to release intracellular contents, including HSV nucleic acids or genetic sequences comprising the UL42 ORF. Sample preparation before amplification may include an optional step of target capture to specifically or non-specifically separate the target nucleic acids from other sample components. Nonspecific target capture methods may involve selective precipitation of nucleic acids from a substantially aqueous mixture, adherence of nucleic acids to a support that is washed to remove other sample components, other methods of physically separating nucleic acids from a mixture that contains HSV nucleic acid and other sample components.

In one embodiment, HSV target nucleic acids are selectively separated from other sample components by specifically hybridizing the HSV target nucleic acid to a capture oligomer specific for HSV to form a target sequence:capture probe complex. The complex is separated from sample components by binding the target:capture probe complex to an immobilized probe, and separating the target:capture probe:immobilized probe complex from the sample, as previously described (U.S. Pat. Nos. 6,110,678; 6,280,952; and 6,534,273). Target capture may occur in a solution phase mixture that contains one or more capture oligonucleotides that hybridize specifically to target nucleic acids under hybridizing conditions, usually at a temperature higher than the Tm of the tail sequence:immobilized probe sequence duplex. The target:capture probe complex is captured by adjusting the hybridization conditions so that the capture probe tail hybridizes to the immobilized probe, and the entire complex on the support is then separated from other sample components. The support with the attached immobilized probe:capture probe:target sequence may be washed one or more times to further remove other sample components. Other embodiments link the immobilized probe to a particulate support, such as a paramagnetic bead, so that particles with the attached target:capture probe:immobilized probe complex may be suspended in a washing solution and retrieved from the washing solution, by using magnetic attraction. To limit the number of handling steps, the target nucleic acid may be amplified by simply mixing the target sequence in the complex on the support with amplification oligonucleotides and proceeding with amplification steps.

Capture probes including a $dT_3A_{30}$ tail portion are suitable for hybridization to a complementary immobilized sequence, whereas capture probes without this tail portion can be used in conjunction with another ligand that is a member of a binding pair (e.g., biotinylated DNA to bind to immobilized avidin or streptavidin). The complex of the capture probe, its target HSV nucleic acid, and an immobilized binding partner or probe facilitate separation of the HSV nucleic acid from other sample components, and optional washing steps may be used to further purify the captured viral nucleic acid.

Amplification of the HSV Target Region

Amplifying the HSV target region using two or more primers may be accomplished using a variety of known nucleic acid amplification reactions. For example, amplification may be achieved using PCR amplification (see, e.g., U.S. Pat. Nos. 4,683,195, 4,683,202, and 4,800,159, Mullis et al.) to produce multiple DNA strands by using thermocycling reactions that separate dsDNA and primers specific for portions of the separated strands to make additional dsDNA molecules by using a DNA polymerase. Well-known variations of the basic PCR method may also be used, e.g., reverse-transcriptase PCR that uses RT to produce a cDNA from an RNA template, and then the DNA is amplified by PCR cycles, or PCR coupled with real-time detection, both of which are sometimes referred to as RT-PCR (e.g., TaqMan One-Step RT-PCR kits, Applied Biosystems, Inc., Foster City, Calif.).

Preferably the amplification step uses a transcription-associated amplification reaction, such as TMA (described in detail in, e.g., U.S. Pat. Nos. 5,399,491 and 5,554,516). A TMA-based assay produces many RNA transcripts (amplicons) from a single copy of target nucleic acid (e.g., RNA), and the amplicons are detected to indicate the presence of the target HSV in the sample. Briefly, in TMA-based assays, a promoter-primer hybridizes specifically to the target sequence and reverse transcriptase (RT) that includes RNaseH activity creates a first strand cDNA by extension from the 3' end of the promoter-primer and digests the template strand. The cDNA is then bound by a second primer and a new strand of DNA is synthesized from the end of the second primer using RT to create a double-stranded DNA (dsDNA) containing a functional promoter sequence. RNA polymerase specific for that promoter binds to the promoter sequence and multiple RNA transcripts are produced, which each can act as a template for additional sequence replication using the same steps used for the initial template. Thus, large amounts of single-stranded amplified product are made using substantially isothermal reaction conditions.

Amplification methods that use TMA amplification may include the following steps. Briefly, a single stranded target nucleic acid—such as RNA—containing the target sequence to be amplified is provided. A first amplification oligomer is brought in contact with that target nucleic acid by hybridizing to the target sequence. The first amplification oligomer may be a primer or a promoter primer. A suitable nucleic acid polymerase then generates a nucleic acid strand amplification product that is complementary to the target nucleic acid target sequence. In the instances where the target nucleic acid is an RNA, the RNA is typically degraded leaving just the newly generated amplification product, which is available for hybridization by a second amplification oligomer. Using a primer as the first amplification oligomer, then the second amplification oligomer is a promoter primer or promoter provider. A suitable nucleic acid polymerase uses the newly generated amplification product to which the promoter-based oligomer is hybridized as a primer to make a complementary strand of the unhybridized promoter sequence. If the second amplification oligomer is a promoter primer, then a complementary copy of the amplification product hybridized by the second amplification oligomer is also generated. The now double stranded promoter sequence of the promoter-based amplification is used by a suitable RNA polymerase to initiate transcription and make RNA transcript amplification products. The first amplification oligomer primer can then hybridize the transcribed amplification products and the steps can repeat. Or, the target nucleic acid is RNA and the first amplification oligomer is a promoter-based amplification oligomer. Here, the promoter based amplification oligomer is a promoter primer. A suitable polymerase makes a first amplification product that is complementary to the RNA target sequence. The RNA target nucleic acid is degraded and a second amplification oligomer is hybridized to the amplification product. A suitable polymerase makes a complement strand, thereby generating a double stranded promoter sequence. Transcription is initiated and RNA is transcribed. The transcribed RNA is complementary to the original target nucleic acid, thus the second amplification oligomer hybridizes again and makes the transcribed RNA double stranded. The RNA is degraded and the remaining DNA strand is hybridized by the first amplification oligomer. The amplification steps can repeat. When the target nucleic acid is DNA the first amplification oligomer is a promoter primer and the second amplification is a primer. Amplification generally proceeds as described above, and as is described in the art. See e.g., U.S. Pat. Nos. 4,868,105; 5,124,246; 5,130,238; 5,399,491; 5,437,990; 5,554,516; and 7,374,885; and PCT Pub. Nos. WO 88/01302; WO 88/10315 and WO 95/03430 describing TMA and other variations of transcription-associated amplification. The amplified products may be detected in real-time during amplification, or at the end of the amplification reaction. Detection may be performed by a number of methods. Probe-based detection methods use an oligonucleotide probe comprising a target hybridizing sequence that binds specifically to a target sequence contained in the amplification products. Detection of a signal resulting from the bound probes indicates the presence of the target nucleic acid in the sample.

Nucleic Acid Detection

Detection of the nucleic acids may be accomplished by a variety of methods. Detection methods may use nucleic acid probes comprising a target-hybridizing sequence that is complementary to a portion of the amplified product and detecting the presence of the probe:product complex, or by using a complex of probes that may amplify the detectable signal associated with the amplified products (e.g., U.S. Pat. Nos. 5,424,413; 5,451,503; and 5,849,481). Directly or indirectly labeled probes that specifically associate with the amplified product provide a detectable signal that indicates the presence of the target nucleic acid in the sample. For example, if the target nucleic acid is HSV (e.g. HSV-1 or HSV-2) RNA, the amplified product will contain a sequence in or complementary to a HSV target sequence. A probe is configured to bind directly or indirectly to a portion of the amplification product to indicate the presence of HSV in the tested sample.

Probes that hybridize to the amplified sequences include hairpin oligonucleotides such as Molecular Torches and linear oligonucleotides that substantially do not form conformations held by intramolecular bonds. Preferably, the probes include labels. Linear probe embodiments may include a chemiluminescent compound as the label, e.g., a chemiluminescent AE compound attached to the probe sequence via a linker (substantially as described in U.S. Pat. Nos. 5,585,481 and 5,639,604, particularly at column 10, line 6 to column 11, line 3, and in Example 8 therein). Examples of labelling positions are a central region of the probe oligomer and near a region of A:T base pairing, at a 3' or 5' terminus of the oligomer, and at or near a mismatch site with a known sequence that is not the desired target sequence. Hairpin or linear probes may be labeled with any of a variety of different types of interacting labels, where one interacting member is usually attached to the 5' end of the probe and the other interacting member is attached to the 3' end of the probe. Dye labeled probes, including dual labeled probes, single labeled probes, AE labeled probes and the like, are generally known. Dual labeled probes can be labeled at one end with a fluorescent label ("F") that absorbs light of a particular wavelength or range and emits light another emission wavelength or range and at the other end with a quencher ("Q") that dampens, partially or completely, signal emitted from the excited F when Q is in proximity with the fluorophore. Such a probe may be referred to as labeled with a fluorescent/quencher (F/Q) pair. One embodiment of a hairpin probe is a "molecular torch" that detects an amplified product to indicate whether a target sequence is present in the sample after the amplification step. A molecular torch probe comprises a target binding domain and a closing domain, as is described above. These domains allow the molecular torch to exist in open and closed conformations, depending on whether the torch is bound to a target. (See, e.g., U.S. Pat. Nos. 6,849,412; 6,835,542; 6,534,274; and 6,361,945). Another hairpin probe embodiment is a "molecular beacon" which is generally described in, e.g., Tyagi et al., 1998, *Nature Biotechnol.* 16:49-53, and U.S. Pat. Nos. 5,118,801 and 5,312,728. Methods for using such hairpin probes to detect the presence of a target sequence are well-known in the art.

One method for detecting HSV sequences may use a transcription-associated amplification together with a molecular torch. The molecular torch is added before or during amplification, allowing detection to be carried out without the addition of other reagents. For example, a molecular torch may be designed so that the Tm of the hybridized target binding region and closing region complex is higher than the amplification reaction temperature, thusly designed to prevent the probe from prematurely binding to amplified target sequences. After an interval of amplification, the mixture is heated to open the torch regions and allow the target binding regions to hybridize to a portion of the amplification products. The solution is then cooled to close any probes not bound to amplified products by allowing the probe target binding and closing regions to hybridize, which effectively closes the label/quencher pair. Detection is then performed to generate and detect signals from only the probes that are hybridized to the amplified target sequences. For example, the mixture containing the F/Q labeled hairpin probe is irradiated with the appropriate excitation light and the emission signal is measured. In other embodiments, the hairpin detection probe is designed so that the amplified products hybridize to the target binding region of the probe during amplification, resulting in changing the hairpin to its open conformation during amplification, and the amplification reaction mixture is irradiated at intervals to detect the emitted signal from the open probes in real time during amplification.

Exemplary probes for the detection of HSV are disclosed in SEQ ID NOs:8, 10, 16, 21, 22, 26, and 27. Advantageously, these probes can be used to discriminate between HSV-1 and HSV-2 nucleic acids since the configuration of the probes utilizes a difference between the nucleic acid sequences from HSV-1 and HSV-2. A detection signal will only be obtained with an HSV-1 probe having a sequence as shown in any one of SEQ ID NOs:8, 10, 21, and 22 when HSV-1 nucleic acid has been amplified and is detected. Likewise, a detection signal will only be obtained with an HSV-2 probe having a sequence as shown in any one of SEQ ID NOs:16, 26, and 27 when HSV-2 nucleic acid has been amplified and is detected.

In a preferred embodiment, the probes for HSV-1 and HSV-2 are labeled with a separately detectable label—such as a 5' fluorophore—and so it is possible to determine if the signal obtained is from an HSV-1 or an HSV-2 probe. In a further preferred embodiment, each of the probes for HSV-1 and each of the probes for HSV-2 are each labeled with a separately detectable label.

Exemplary Method for the Amplification and Detection of HSV Nucleic Acid

In general, methods used to demonstrate amplification and detection of HSV nucleic acid by using the compositions described herein involve the following steps. HSV RNA is separated from other sample components by using a method that attaches the target HSV nucleic acid to a solid support that is separated from other sample components. In preferred embodiments, viral RNA is separated from other sample components by using a target-capture system that includes a target-specific capture probe for the HSV viral analyte (e.g., using methods steps described in U.S. Pat. Nos. 6,110,678, 6,280,952 and 6,534,273), or a non-specific method for separation of nucleic acids was used (U.S. Pat. No. 5,234,809). Non-specific separation of viral RNA from other sample components is performed by adhering nucleic acids reversibly to a solid support, followed by washing and elution of the adhered nucleic acids into a substantially aqueous solution (e.g., using a QIAAMP™ Viral RNA Mini kit, Qiagen Inc.). Isolated HSV nucleic acid is amplified for specific target sequences contained in the genome by using TMA amplification, and the amplification products are detected after completion of the amplification reaction. Signal can be detected by using a system that incubates the reactions and detects fluorescence at different wavelengths (e.g., using a DNA Engine OPTICON™ 2 system or CHROMO4™ Real-Time PCR Detector, Bio-Rad Laboratories, Inc., Hercules, Calif.).

Real-time TMA-based assays may also be used. These assays are typically performed in reaction mixture that contains the analyte nucleic acid, amplification reagent (e.g., APTIMA™ reagent, Gen-Probe Incorporated, San Diego, Calif.), a T7 promoter primer (e.g., about 9 pmol/reaction), a second primer without a promoter (e.g., about 15 pmol/reaction), and a detection probe (e.g., about 0.2-0.3 pmol/reaction) for amplicon detection, in a 40.micro.1 reaction (in a well of a standard 96-well plate, covered with a layer of inert oil or sealing device to prevent evaporation). The mixture of target nucleic acid, primers, and probe may be incubated at about 60.deg.0 for about 10 min, cooled to about 42.deg.0 for about 5 min, and then enzyme reagent containing RT and T7 RNA polymerase is added, the mixture is mixed (e.g., 30 sec vortex) and then incubated at about 42.deg.0 for about 75-100 min for isothermal amplification during which detection of fluorescence is performed either during the reaction (e.g., every 3 seconds) or at the end of the reaction. Amplification and detection steps may be performed using an incubation and open channel fluorimeter (e.g., CHROMO4™, Bio-Rad Laboratories, Inc.) for real-time two-color fluorescence detection. The assays may include an IC, as described above, i.e., a reaction mixture included primers and probe for the target HSV nucleic acid and IC-specific primers and probe, each probe labeled with a separately detectable 5' fluorophore. Real-time fluorescence signals are analyzed and a detection signal (time of emergence) is calculated. Time of emergence is calculated, e.g., by using a method that analyzes the detected signals (relative fluorescence units or RFU) relative to the signal detection times (RFU(t) data points) to determine a time of emergence ("T-time"), which is the time at which a RFU(t) data point reaches a predefined threshold value (described in detail in U.S. application Ser. No. 60/659,874, Scalese et al., filed Mar. 10, 2005; and US published application US2007-0243600). Briefly, RFU(t) data is treated to subtract background signal ("noise" level) and curves (RFU vs time) is normalized to optimize curve fit for data between predetermined minimum and maximum points. In general, samples that contain a higher analyte concentration result in a steeper curve slope and an earlier time of emergence. Average times of emergence are compared to determine the relative efficiencies of the different assay conditions, e.g., to compare for a single known amount of analyte, the time of emergence detected by using a PCR-based assay compared to using a TMA-based assay.

Correlation of Detection of a Target Sequence with Diagnosis

The detection of amplified target sequences characteristic of HSV-1 in a biological sample from an individual is indicative of infection by HSV-1. Detection of amplified target sequences characteristic of HSV-2 in a biological sample from an individual is indicative of infection by HSV-2. Detection of both targets in the same sample is indicative of infection by both HSV-1 and HSV-2.

V. Reaction Mixtures and Kits

Also provided by the subject invention is a reaction mixture for amplification and/or detection of an HSV-1 and/or HSV-2 target nucleic acid. A reaction mixture in accordance with the present invention at least comprises one or more of the following: one or more oligomer combination(s) as described herein for amplification of an HSV-1 and/or HSV-2 target nucleic acid; and one or more detection probe oligomer(s) as described herein for determining the presence or absence of HSV-1 and/or HSV-2 amplification product(s). The reaction mixture may further include a number of optional components such as, for example, arrays of capture probe nucleic acids. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzyme(s) (e.g., DNA polymerase, reverse transcriptase, RNA polymerase), and may include test sample components, in which an HSV-1 and/or HSV-2 target nucleic acid may or may not be present. In addition, for a reaction mixture that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture).

Also provided by the subject invention are kits for practicing the methods as described herein. A kit in accordance with the present invention at least comprises one or more of the following: one or more oligomer combination(s) as described herein for amplification of an HSV-1 and/or HSV-2 target nucleic acid; and one or more detection probe oligomer(s) as described herein for determining the presence or absence of HSV-1 and/or HSV-2 amplification product(s). The kits may further include a number of optional components such as, for example, arrays of capture probe nucleic acids. Other reagents that may be present in the kits include reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzyme(s) (e.g., DNA polymerase, reverse transcriptase, RNA polymerase). Oligomers as described herein may be packaged in a variety of different embodiments, and those skilled in the art will appreciate that the invention embraces many different kit configurations. For example, a kit may include amplification oligomers for only one of an HSV-1 and HSV-2 target region, or it may include amplification oligomers for both HSV-1 and HSV-2 target regions. In addition, for a kit that includes a detection probe together with an amplification oligomer combination, selection of amplification oligomers and detection probe oligomers for a kit are linked by a common target region (i.e., the kit will include a probe that binds to a sequence amplifiable by an amplification oligomer combination of the kit). Such a kit may comprise containers, each with one or more of the various oligomers optionally together with one or more of the reagents (e.g., enzymes) required to perform the methods described herein. The components of the kit may be supplied in concentrated form. A set of instructions for using the components of the kit will also typically be included, where the instructions may be associated with a package insert and/or the packaging of the kit or the components thereof. Where the kit comprises combinations of oligomers then the individual oligomers may be provided in individual form, with appropriate instructions for mixing same, or combinations thereof that are ready mixed.

EXAMPLES

Example 1

Reagents for TMA-Based Assays

Unless otherwise specified, reagents commonly used in the TMA-based assays described herein include the following. Sample transport reagent: 110 mM lithium lauryl sulfate (LLS), 15 mM NaH$_2$PO$_4$, 15 mM Na$_2$HPO$_4$, 1 mM EDTA, 1 mM EGTA, pH 6.7. Lysis buffer: 790 mM HEPES, 230 mM succinic acid, 10% (w/v) LLS, and 680 mM LiOH monohydrate. Target Capture Reagent (TCR): 250 mM HEPES, 1.88 M LiCl, 310 mM LiOH, 100 mM EDTA, pH 6.4, and 250.micro.g/ml of paramagnetic particles (0.7-1.05 micron particles, Sera-Mag™ MG-CM) with (dT)$_{14}$ oligomers covalently bound thereto. Wash Solution: 10 mM HEPES, 150 mM NaCl, 6.5 mM NaOH, 1 mM EDTA, 0.3% (v/v) ethanol, 0.02% (w/v) methylparaben, 0.01% (w/v) propylparaben, and 0.1% (w/v) sodium lauryl sulfate, pH 7.5. Amplification reagent: a concentrated solution containing 125 mM HEPES, 26.7 mM rATP, 33.3 mM rGTP, 5 mM each of rCTP and UTP, 1.33 mM each of dATP, dCTP, dGTP and dTTP, 8% (w/v) trehalose, pH 7.7, to which primers and probes may be added. TMA Enzymes: per reaction about 90 U/.micro.1 of MMLV reverse transcriptase (RT) and about 20 U/.micro.1 of T7 RNA polymerase per reaction (where 1 U of RT incorporates 1 nmol of dTTP in 10 min at 37.deg.0 using 200-400.micro.M oligo-dT-primed polyA-template, and 1 U of T7 RNA polymerase incorporates 1 nmol of ATP into RNA in 1 hr at 37.deg.0 using a T7 promoter in DNA template). Probe Reagent for AE-labeled probes: a solution of (a) 100 mM Li-succinate, 3% (w/v) LLS, 10 mM mercaptoethanesulfonate (MES), and 3% (w/v) polyvinylpyrrolidon, or (b) 100 mM Li-succinate, 0.1% (w/v) LLS, and 10 mM MES. Hybridization Reagent: (C-type) 100 mM succinic acid, 2% (w/v) LLS, 100 mM LiOH, 15 mM aldrithiol-2, 1.2 M LiCl, 20 mM EDTA, and 3.0% (v/v) ethanol, pH 4.7. Selection Reagent: 600 mM boric acid, 182.5 mM NaOH, 1% (v/v) octoxynol (TRITON® X-100), pH 8.5 to 9.2, to hydrolyze AE labels on unbound oligomers. Detection Reagents for AE labels are Detect Reagent I: 1 mM nitric acid and 32 mM H$_2$O$_2$, and Detect Reagent II: 1.5 M NaOH (see U.S. Pat. Nos. 5,283,174, 5,656,744, and 5,658,737).

Example 2

Sensitivity and Specificity Testing of Oligomer Combinations for Amplification and Detection of HSV-1 and HSV-2 Target Nucleic Acid Analytical sensitivity testing was evaluated using in vitro RNA transcript (IVT) synthesized from cloned HSV1 and 2 Us8.5 and UL42 RNAs. Target IVTs were spiked into APTIMA Specimen Transport Medium (STM, Gen-Probe Incorporated, USA) to concentrations of 3, 10, 30, 100, 300 and 1000 copies per reaction (cpr). For each monoplex assay, 15 replicates of each concentration were tested on the TIGRIS® DTS® System (Gen-Probe Incorporated). A Probit analysis was performed to determine the 95% and 50% detection levels for each of the monoplex assays. The different combinations of amplification oligomers and detection probes tested in this experiment are shown in Table 10.

TABLE 1

Different combinations of amplification oligomers and detection probes tested in Example 2

| Condition | Primer | Promoter primer | Detection probe |
|---|---|---|---|
| 5 | SEQ ID NO: 56 | SEQ ID NO: 55 | SEQ ID NO: 57 |
| 6 | SEQ ID NO: 56 | SEQ ID NO: 58 | SEQ ID NO: 59 |
| 7 | SEQ ID NO: 60 | SEQ ID NO: 55 | SEQ ID NO: 59 |
| 8 | SEQ ID NO: 62 | SEQ ID NO: 61 | SEQ ID NO: 63 |
| 9 | SEQ ID NO: 64 | SEQ ID NO: 61 | SEQ ID NO: 65 |
| 10 | SEQ ID NO: 62 | SEQ ID NO: 66 | SEQ ID NO: 65 |
| 11 | SEQ ID NO: 7 | SEQ ID NO: 5 | SEQ ID NO: 8 |
| 12 | SEQ ID NO: 9 | SEQ ID NO: 5 | SEQ ID NO: 10 |
| 13 | SEQ ID NO: 7 | SEQ ID NO: 11 | SEQ ID NO: 8 |
| 14 | SEQ ID NO: 15 | SEQ ID NO: 13 | SEQ ID NO: 16 |

The assays used forward primers (9 pmol/reaction), reverse promoter primers (15 pmol/reaction) and a chemiluminescent acridinium ester labeled detection probe (0.32 pmol/reaction) in a TMA reaction performed substantially as described above.

Exemplary results from the tests are shown in Tables 2 to 5 and are expressed as RLU for each of the conditions tested.

TABLE 2

| HSV-1 US8.5 and condition 5 | | | | | | | |
|---|---|---|---|---|---|---|---|
| | 0 copies | 3 copies | 10 copies | 30 copies | 100 copies | 300 copies | 1000 copies |
| number positive | 0 | 5 | 4 | 8 | 15 | 15 | 15 |
| percent positive | 0 | 33 | 27 | 53 | 100 | 100 | 100 |
| AVG RLU | 2,400 | 465,933 | 358,867 | 920,600 | 1,770,200 | 1,792,800 | 1,854,800 |

TABLE 3

| HSV-2 US8.5 and condition 8 | | | | | | | |
|---|---|---|---|---|---|---|---|
| | 0 copies | 3 copies | 10 copies | 30 copies | 100 copies | 300 copies | 1000 copies |
| Number positive | 0 | 4 | 10 | 14 | 15 | 15 | 15 |
| Percent positivity | 0 | 27 | 67 | 93 | 100 | 100 | 100 |
| AVG RLU | 1,733 | 91,867 | 305,333 | 743,200 | 1,342,200 | 1,545,133 | 1,551,067 |

TABLE 4

| HSV-1 UL42 and condition 11 | | | | | | | |
|---|---|---|---|---|---|---|---|
| | 0 copies | 3 copies | 10 copies | 30 copies | 100 copies | 300 copies | 1000 copies |
| Number positive | 0 | 1 | 2 | 11 | 13 | 15 | 15 |
| Percent positivity | 0 | 7 | 13 | 73 | 87 | 100 | 100 |
| AVG RLU | 2,293 | 15,085 | 21,756 | 735,712 | 839,977 | 1,219,166 | 1,348,715 |

TABLE 5

| HSV-2 UL42 and condition 14 | | | | | | | |
|---|---|---|---|---|---|---|---|
| | 0 copies | 3 copies | 10 copies | 30 copies | 100 copies | 300 copies | 1000 copies |
| number positive | 0 | 0 | 6 | 12 | 15 | 15 | 15 |
| percent positivity | 0 | 0 | 40 | 80 | 100 | 100 | 100 |
| AVG RLU | 16,447 | 16,501 | 356,355 | 519,721 | 897,714 | 1,020,993 | 1,029,458 |

These data show that conditions 5, 8, 11 and 14 are capable of detecting HSV-1 and HSV-2 target nucleic acids. Table 6 further illustrates using conditions 5 and 8 that there is no crossreactivity with these oligomers combinations to non-target HSV US8.5. Reactions were set up as is generally shown above using the condition 5 and condition 8 oligomer combinations. 1×10.sup.8 copies of HSV-1 US8.5 IVT was spiked into STM and amplification and detection was performed using condition 8 oligomers (HSV-2 US8.5). Likewise, 1×10.sup.8 copies of HSV-2 US8.5 IVT was spiked into STM and amplification and detection reaction was performed using condition 5 oligomers (HSV-1 US8.5).

TABLE 6

| Crossreactivity | | |
|---|---|---|
| | Crossreactivity HSV-1 US8.5 IVT HSV-2 Condition 8 | Crossreactivity HSV-2 US8.5 IVT HSV-1 Condition 5 |
| number positive | 0 | 0 |
| percent positivity | 0 | 0 |
| AVG RLU | 4,000 | 3,133 |

Example 3

Clinical Sensitivity of a TMA Assay for Detecting HSV-1 and HSV-2 Target Nucleic Acids Clinical sensitivity and specificity of a TMA assays was evaluated by testing anogenital swab samples (n=406, Wishard Memorial Hospital) collected in viral transport medium (VTM). TMA detection results were compared to ELVIS culture reference standard. VTM-based samples were diluted ½₀ in STM and tested on the TIGRIS® DTS® System (Gen-Probe Incorporated, USA). Samples yielding negative TMA results were retested at lower dilutions. For both US8.5 and UL42 RNA targets, combined results of the HSV-1 and HSV-2 TMA assays were compared to ELVIS culture results as the reference standard to calculate sensitivity and specificity. PCR-sequencing assays targeting HSV½ Us8.5 and UL42 DNA were used to resolve samples yielding discordant results between ELVIS and the TMA assays. PCR reactions were generally prepared as 50 microliter reactions containing 1× ABI PCR buffer (Life Technologies, Inc., USA), 1.5 mM magnesium, 0.4 microM of dNTPs and each oligomer, DMSO, polymerase, 5 microliters of sample in STM and water to 50 microliters total volume. For the PCR assays, amplification products were then run on an agarose gel, the bands were excised and each excised band was separately sequenced in a sequencing reaction do identify the amplified target nucleic acid. Oligomer combinations are presented in Table 7.

TABLE 7

| Different combinations of amplification oligomers and detection probes tested in Example 3 | | | |
|---|---|---|---|
| Condition | Primer | Promoter primer | Detection probe |
| 5 | SEQ ID NO: 56 | SEQ ID NO: 55 | SEQ ID NO: 57 |
| 8 | SEQ ID NO: 62 | SEQ ID NO: 61 | SEQ ID NO: 63 |
| 11 | SEQ ID NO: 7 | SEQ ID NO: 5 | SEQ ID NO: 8 |

TABLE 7-continued

Different combinations of amplification oligomers
and detection probes tested in Example 3

| Condition | Primer | Promoter primer | Detection probe |
|---|---|---|---|
| 14 | SEQ ID NO: 15 | SEQ ID NO: 13 | SEQ ID NO: 16 |
| 15 | SEQ ID NO: 67 | SEQ ID NO: 68* | None* |

*condition 15 is a PCR reaction. Thus, SEQ ID NO: 68 is a primer without a promoter sequence and there was no probe in this PCR reaction.

HSV TMA assay analytical sensitivity for HSV viral RNAs showed 95% limit of detection results as follows: HSV-1 US8.5, 125 copies per reaction: HSV-2 US8.5, 63 copies per reaction; HSV-1 UL42, 71 copies per reaction; and HSV-2 UL42, 17 copies per reaction. For 50% limit of detection results were 16, 14, 7 and 5 copies per reaction, respectively. US8.5 and UL42 targets were also evaluated for TMA inter-assay agreement, which for HSV-1 UL42 and HSV-1 US8.5 the overall agreement was 98.5% (95% CI: 96.8-99.3), and for HSV-2 UL42 and HSV-2 US8.5 the overall agreement was 99.0% (95% CI: 97.5-99.6). TMA assay results were evaluated for assay performance relative to ELVIS Culture results, which for combined HSV-½ UL42 the results data is illustrated in Table 8 and for combined HSV-½ US8.5 the results data is illustrated in Table 9. Discordant TMA/ELVIS results were resolved using PCR (result data in Table 10).

TABLE 8

Clinical performance of combined HSV1/2 UL42 TMA Assays

| HSV1/2 UL42 | ELVIS Culture Result | | |
|---|---|---|---|
| TMA Assays | Pos | Neg | Total |
| Pos | 180 | 32 | 212 |
| Neg | 4 | 190 | 194 |
| Total | 184 | 222 | 406 |

Sensitivity (95% CI) 97.8% 94.5-99.2
Specificity (95% CI) 85.6% 80.4-89.6

TABLE 9

Clinical performance of combined HSV1/2 Us8.5 TMA Assays

| HSV1/2 Us8.5 | ELVIS Culture Result | | |
|---|---|---|---|
| TMA Assays | Pos | Neg | Total |
| Pos | 181 | 34 | 215 |
| Neg | 3 | 188 | 191 |
| Total | 184 | 222 | 406 |

Sensitivity (95% CI) 98.4% (95.3-99.4)
Specificity (95% CI) 84.7% (79.4-88.8)

TABLE 10

Resolution of TMA Assay/ELVIS Culture Discordant Results

| TMA Assay | Original Test Results | # tested by PCR | PCR+ | PCR− |
|---|---|---|---|---|
| HSV1/2 Us8.5 | TMA+/ELVIS− (n = 34) | 30 | 11 | 19 |
| | TMA−/ELVIS+ (n = 3) | 3 | 0 | 3 |

These data show that UL42 and US8.5 TMA assays have excellent overall agreement for detection of Herpes simplex virus 1 and 2 genital infections. These data further show that TMA assays for HSV1 and 2 viral RNAs are more sensitive than ELVIS culture and may be more sensitive than PCR for detection of HSV1 and 2 infections.

Example 4

Triplex Amplification and Real-Time Detection Reaction for Identifying HSV-1 and/or HSV-2 in Clinical Specimen Three hundred HSV clinical samples were obtained from Wishard Health Services (Indianapolis, Ind.), each sample being identified as culture positive or culture negative. The clinical samples were received in Remel M4RT liquid medium (cat #R12505, Thermo Scientific, Lenexa, KS) or an equivalent viral culture medium, were then diluted 1:20 (2 of the 300 were diluted 1:40) in sample transport reagent and then tested in a triplex (HSV-1, HSV-2 and internal control) amplification and real-time detection assay (n=300). Internal control was a non-HSV nucleic acid target. Positive controls were in vitro transcripts expressed from a vector containing an HSV-1 or HSV-2 target region obtained from a clinical specimen shown by ELVIS to be HSV-1 or HSV-2 positive, respectively. Samples with an RFU range value >1000 and a curve fit slope of 0.015 or greater were identified as HSV positive samples (US App No. 2006/0276972).

The triplex amplification and real-time detection reactions were performed as TMA reaction using a Panther instrument Platform (Gen-Probe Incorporated, San Diego, Calif.), wherein each amplification and detection reaction was configured to amplify and detect HSV-1, HSV-2 and a nucleic acid internal control. Target capture was performed using target capture reagent containing target capture oligomers (SEQ ID NO:17, for capture of HSV-1 and -2 and a target capture oligomer for capture of the internal control—not shown), and containing a separate T7 primer for each of HSV-1, HSV-2 and the internal control (SEQ ID NO:19 for HSV-1, SEQ ID NO:23 for HSV-2, T7 primer for the internal control). The amplification reagent was divided into two separate reagents; the first amplification reagent containing the non-T7 primers; and the second amplification reagent containing the same T7 primers as the target capture reagent and containing detection probes. Non-T7 primers were SEQ ID NO:7 for HSV-1, SEQ ID NO:25 for HSV-2 and a primer for the internal control. Detection probes were configured as torches (SEQ ID NO:21 for HSV-1, SEQ ID NO:26 for HSV-2 and an internal control, all differently labeled for distinction during a detection reaction (e.g., FAM, ROX, HEX)).

Target capture was performed generally described for the APTIMA Combo 2 Assay on PANTHER (Gen-Probe Incorporated, Cat #302923). Briefly, lysed target is combined with target capture oligomers, magnetic beads joined to immobilized probes, and T7 primers. Reaction conditions were provided so to hybridize the target capture oligomers and the T7 primers to their intended targets, and to hybridize the target capture oligomer to an immobilized probe. A series of wash steps were performed to remove cellular components, culture and transport medium and the like. Following the wash step, a first amplification reagent was added to the washed and captured taregt nucleic acids. The first amplification reagent contained only non-T7 primers. There was no primer-annealing step prior to enzyme addition since the T7 primers were already bound to the target from the target capture step. Initiation of amplification occured at addition of enzyme and then was followed by a 5-minute incubation step at 42° C. The second amplification reagent containing T7 primers and torches as detection probes was added to the first amplification reagent after a 5-minute 42.deg.C incubation reaction. Real-time detection occurred during this step measured by 3 separate fluorometers used to detect FAM, ROX, and HEX labels on each of the different detection probes. Reaction readings occurred for 53 minutes. Agreement between this HSV assay and ELVIS culture results is shown below in Table 11.

TABLE 11

Agreement of HSV Triplex Amplification and Real-Time Detection Assay to ELVIS Culture Results.

| | ELVIS Assay Positive | ELVIS Assay Negative | Total Samples | % Agreement (95% Confidence Interval) |
|---|---|---|---|---|
| HSV Triplex Positive | 157 | 11 | 168 | 91.3% (86.1-94.6) |
| HSV Triplex Negative | 15 | 117 | 132 | 91.4% (85.3-95.1) |
| Total | 172 | 128 | 300 | 91.3% (87.6-94.0) |

Table 11 shows that there is strong agreement between these real-time amplification and detection assay results and ELVIS culture results for the tested clinical samples. Of the 300 samples tested, only 26 discordant results were observed for an overall agreement of 91.3% (95% CI: 87.6%-94.0%). Positive agreement was 91.3% (95% CI: 86.1%-94.6%). Negative agreement was 91.4% (95% CI: 85.3%-95.1%). It is notable that both of the samples tested at a 1:40 dilution provided amplification and detection results that were concordant with their corresponding ELVIS results. Strong positive agreement between the instant amplification and detection assay results and ELVIS culture results shows that the instant assay accurately detects the presence of HSV-1 and HSV-2 when targeting HSV RNA.

Example 5

Target Capture Oligomer Evaluation

The experiment described in this example demonstrates improved sensitivity for HSV at lower copy levels using target capture oligomer HSV UL42 878-897 TC_methoxy (SEQ ID NO:69) or HSV UL42 881-900 TC_methoxy in addition to target capture oligomer HSV UL42 544 TC_methoxy (SEQ ID NO:17).

The basic protocol used for running HSV Triplex kits on the PANTHER instrument was as follows:

1. Aliquot reagents into appropriate sized containers using serological pipettes and L1000 or L200 if necessary. See calculations table for reagent volumes.
    a. AMP1/AMP2:
        i. 2× Midpoint AMP: Add half of the total volume of AMP1
        ii. Nuclease free water: Add half of the total volume of AMP1 less the total volume of oligos to be spiked
            1. Oligos are diluted in nuclease free water. This will create a 1× solution of midpoint AMP at the desired concentration of oligos.
    b. TCR (Target Capture Reagent):
        i. TCR: Add total volume of TCR less the total volume of oligos to be spiked and IC IVT (internal control in vitro transcript)
2. Spike oligos using L200 or L20:
    a. Thaw oligos and keep on ice when not in use.
    b. Mix oligos thoroughly before spiking
    c. Add required volume to appropriate reagent as determined by desired concentrations. See calculations table for oligo concentrations and spike volumes.
3. Spike IC IVT using L200 or L20:
    a. Spike IC IVT into TCR
4. Mix reagents thoroughly
5. Reconstitute enzyme, re-label bottle(s)
6. Pull appropriate panels from −20° C. freezer and thaw in room temperature water bath. Invert tubes several times when thawed.
7. Prep and Prime PANTHER instrument
8. Load reagents, samples into PANTHER racks
9. Load reagents, samples onto PANTHER and select the appropriate sequence file and rep number
10. Feed PANTHER tips and MTUs (multi-tube units) as necessary
11. Retrieve data

TABLE 12

Oligos and Their Respective Concentrations

| Oligo Type | Oligo Name | pmol/μg | pmol/rxn | pmol/μl (50 μl rxn vol) |
|---|---|---|---|---|
| | AMP1 | | | |
| Non-T7 | GIC 4102 nonT7 | 169.93 | 2.25 | 0.05 |
| Non-T7 | HSV1 602 nonT7 (SEQ ID NO: 7) | 147.40 | 25.00 | 0.5 |
| Non-T7 | HSV2 UL42 774-791 nT7 (SEQ ID NO: 25) | 184.11 | 40.00 | 0.8 |
| | AMP2/Promoter | | | |
| T7 | T7 GIC (−) 4203 | 66.08 | 3.75 | 0.15 |
| Torch | TRU TMA GIC 4180-4197 torch (−) 5A3R | 104.91 | 11.25 | 0.45 |
| T7 | HSV1 UL42 688-709 T7 (SEQ ID NO: 19) | 66.44 | 25.00 | 1 |

TABLE 12-continued

Oligos and Their Respective Concentrations

| Oligo Type | Oligo Name | pmol/μg | pmol/rxn | pmol/μl (50 μl rxn vol) |
|---|---|---|---|---|
| Torch | HSV1 UL42 664au C9(19, 20) 5H3D 6st(+) (SEQ ID NO: 21) | N/A | 11.00 | 0.44 |
| T7 | HSV2 UL42 829-847 T7 (SEQ ID NO: 23) | 70.27 | 40.00 | 1.6 |
| Torch | HSV2 UL42 803-822 C9(20, 21) fam 5st (SEQ ID NO: 26) | 104.88 | 11.00 | 0.44 |
| TCR | | | | |
| T7 | T7 GIC (−) 4203 | 66.08 | 1.88 | 0.02 |
| TCO | MUIC Cap 4277 dT3A30 | 55.1 | 4.00 | 0.04 |
| T7 | HSV1 UL42 688-709 T7 (SEQ ID NO: 19) | 66.44 | 5.00 | 0.05 |
| T7 | HSV2 UL42 829-847 T7 (SEQ ID NO: 23) | 70.27 | 10.00 | 0.10 |
| TCO | HSV UL42 544 TC_methoxy (SEQ ID NO: 17) | 58.7 | 7.00 | 0.07 |
| TCO | HSV UL42 878-897 TC_methoxy (SEQ ID NO: 69) | 58.53 | 7.00 | 0.07 |
| TCO | HSV UL42 881-900 TC_methoxy (SEQ ID NO: 71) | 58.67 | 7.00 | 0.07 |

Bulks of AMP1 and AMP2 were built with enough volume for 3.5 100 reaction test ("100-test") kits, according to reagent calculation sheet, using the oligos and the concentrations in Table 12 above. Each bulk was then split into 3 kits and was paired with a different TCR. Enough TCR was built for 3.5 kits and spiked with all common oligos and IC IVT (in vitro transcript). TCR was then split into 3 25 ml aliquots and 2 were spiked with additional TCOs (see Table 13 below). IC IVT was spiked at $5\times10^3$ cpr. Experiment was run on PP115.

TABLE 13

TCR Conditions

| Kit | Oligo Name | pmol/rxn | Oligo Name | pmol/rxn |
|---|---|---|---|---|
| Kit 1 (Control) | HSV UL42 544 TC_methoxy (SEQ ID NO: 17) | 7.00 | | |
| Kit 2 (Condition 1) | HSV UL42 544 TC_methoxy (SEQ ID NO: 17) | 7.00 | HSV UL42 878-897 TC_methoxy (SEQ ID NO: 69) | 7.00 |
| Kit 3 (Condition 2) | HSV UL42 544 TC_methoxy (SEQ ID NO: 17) | 7.00 | HSV UL42 881-900 TC_methoxy (SEQ ID NO: 71) | 7.00 |

Because this experiment was performed to confirm results obtained in previous experiments and provide additional information, a higher number of replicates was tested at lower copy levels. This experiment was also intended to focus on HSV2 sensitivity, so more HSV2 replicates were tested than HSV1.

TABLE 14

Replicates Tested Per Analyte

| Copy level (cpr of IVT in STM) | HSV1 replicates | HSV2 replicates |
|---|---|---|
| 0 | 0 | 5 |
| 10 | 10 | 30 |
| 30 | 10 | 30 |
| 100 | 5 | 10 |

Results of the assay are summarized below in Tables 15 and 16.

TABLE 15

Results for FAM Channel (HSV2)

| Row Labels | # of Reps | % Pos when Tslope >.02 | Avg Ttime of Pos | Avg Tslope of Pos | Avg RFURange of Pos | Avg RFURange of Neg |
|---|---|---|---|---|---|---|
| HSV Triplex: 544TC_HSV1 Panel | | | | | | |
| 10 CPR | 10 | 0% | 0 | 0 | 0 | 430 |
| 30 CPR | 10 | 0% | 0 | 0 | 0 | 471 |
| 100 CPR | 5 | 0% | 0 | 0 | 0 | 537 |
| HSV Triplex: 544TC_HSV2 Panel | | | | | | |
| 0 CPR | 5 | 0% | 0 | 0 | 0 | 198 |
| 10 CPR | 30 | 23% | 18.59 | 0.0462 | 12786 | 195 |
| 30 CPR | 30 | 17% | 18.55 | 0.0429 | 11618 | 191 |
| 100 CPR | 10 | 100% | 17.31 | 0.0611 | 12666 | 0 |

TABLE 15-continued

Results for FAM Channel (HSV2)

| Row Labels | # of Reps | % Pos when Tslope >.02 | Avg Ttime of Pos | Avg Tslope of Pos | Avg RFURange of Pos | Avg RFURange of Neg |
|---|---|---|---|---|---|---|
| HSV Triplex: 544TC + 878TC_HSV1 Panel | | | | | | |
| 10 CPR | 10 | 0% | 0.00 | 0.0000 | 0 | 422 |
| 30 CPR | 10 | 0% | 0.00 | 0.0000 | 0 | 471 |
| 100 CPR | 5 | 0% | 0.00 | 0.0000 | 0 | 467 |
| HSV Triplex: 544TC + 878TC_HSV2 Panel | | | | | | |
| 0 CPR | 5 | 0% | 0.00 | 0.0000 | 0 | 242 |
| 10 CPR | 30 | 90% | 17.51 | 0.0574 | 12667 | 200 |
| 30 CPR | 30 | 100% | 15.74 | 0.0860 | 12815 | 0 |
| 100 CPR | 10 | 100% | 14.20 | 0.1144 | 13022 | 0 |
| HSV Triplex: 544TC + 881TC_HSV1 Panel | | | | | | |
| 10 CPR | 10 | 0% | 0.00 | 0.0000 | 0 | 410 |
| 30 CPR | 10 | 0% | 0.00 | 0.0000 | 0 | 458 |
| 100 CPR | 5 | 0% | 0.00 | 0.0000 | 0 | 467 |
| HSV Triplex: 544TC + 881TC_HSV2 Panel | | | | | | |
| 0 CPR | 5 | 0% | 0.00 | 0.0000 | 0 | 224 |
| 10 CPR | 30 | 77% | 17.66 | 0.0546 | 12704 | 184 |
| 30 CPR | 30 | 97% | 15.87 | 0.0801 | 12858 | 238 |
| 100 CPR | 10 | 100% | 14.57 | 0.1147 | 12819 | 0 |

The HSV1 panel performed as expected in this channel; no positives. 10 reps of the Control (544TC_me alone) at 30cpr were invalidated due to sample volume error. However, because the 10 cpr and the 100 cpr performed as expected, it was determined that this was not significant enough to require a repeat experiment. The addition of a TCO closer to the HSV2 AMP region significantly improves HSV2 sensitivity. 878TC_me and 881TC_me perform both increase Ttime and Tslope of positives. However, in this experiment, it was determined that 878TC_me gives better sensitivity at 10 and 30 CPR than does 881TC_me.

The addition of another TCO also increases the sensitivity of HSV1 at lower copy levels (See Table 16).

TABLE 16

Results for HEX Channel (HSV1)

| Row Labels | # of Reps | % Pos when Tslope >.015 | Avg Ttime of Pos | Avg Tslope of Pos | Avg RFURange of Pos | Avg RFURange of Neg |
|---|---|---|---|---|---|---|
| HSV Triplex: 544TC_HSV1 Panel | | | | | | |
| 10 CPR | 10 | 60% | 20.78 | 0.0343 | 5735 | 253 |
| 30 CPR | 10 | 90% | 18.05 | 0.0499 | 6213 | 250 |
| 100 CPR | 5 | 100% | 16.39 | 0.0694 | 6342 | 0 |
| HSV Triplex: 544TC_HSV2 Panel | | | | | | |
| 0 CPR | 5 | 0% | 0.00 | 0.0000 | 0 | 234 |
| 10 CPR | 30 | 0% | 0.00 | 0.0000 | 0 | 233 |
| 30 CPR | 30 | 0% | 0.00 | 0.0000 | 0 | 242 |
| 100 CPR | 10 | 0% | 0.00 | 0.0000 | 0 | 212 |
| HSV Triplex: 544TC + 878TC_HSV1 Panel | | | | | | |
| 10 CPR | 10 | 100% | 20.55 | 0.0389 | 5827 | 0 |
| 30 CPR | 10 | 100% | 17.97 | 0.0621 | 6323 | 0 |
| 100 CPR | 5 | 100% | 15.30 | 0.0946 | 6489 | 0 |
| HSV Triplex: 544TC + 878TC_HSV2 Panel | | | | | | |
| 0 CPR | 5 | 0% | 0.00 | 0.0000 | 0 | 247 |
| 10 CPR | 30 | 0% | 0.00 | 0.0000 | 0 | 200 |
| 30 CPR | 30 | 0% | 0.00 | 0.0000 | 0 | 205 |
| 100 CPR | 10 | 0% | 0.00 | 0.0000 | 0 | 255 |
| HSV Triplex: 544TC + 881TC_HSV1 Panel | | | | | | |
| 10 CPR | 10 | 70% | 19.02 | 0.0467 | 6215 | 255 |
| 30 CPR | 10 | 100% | 18.51 | 0.0529 | 6036 | 0 |
| 100 CPR | 5 | 100% | 15.62 | 0.0862 | 6502 | 0 |
| HSV Triplex: 544TC + 881TC_HSV2 Panel | | | | | | |
| 0 CPR | 5 | 0% | 0 | 0 | 0 | 254 |
| 10 CPR | 30 | 0% | 0 | 0 | 0 | 211 |
| 30 CPR | 30 | 0% | 0 | 0 | 0 | 219 |
| 100 CPR | 10 | 0% | 0 | 0 | 0 | 221 |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

SEQUENCES

TABLE 17

Exemplary Oligomer Sequences, Reference Sequences, and Regions

| SEQ ID NO: | Sequence 5'→3' | Description |
| --- | --- | --- |
| 1 | GenBank Accession No. GU734771.1 (GI:290766003), nucleotide positions 92,815-94,534 | HSV-1 UL42 reference sequence |
| 2 | GenBank Accession No. Z86099.2 (GI:6572414), nucleotide positions 93,769-95,181 | HSV-2 UL42 reference sequence |
| 3 | GTACTGGTTGGCGCGAAACATTTAAAAAAAAAAAAAAAAAAAAAAAAAAAA | Target capture oligomer (HSV UL42) |
| 4 | GTACTGGTTGGCGCGAAACA | Target hybridizing sequence of SEQ ID NO: 3 |
| 5 | aatttaatacgactcactatagggagaTTCCCTGGGGAACCAGCACCACA | T7 amp oligomer (HSV1 UL42) |
| 6 | TTCCCTGGGGAACCAGCACCACA | Target hybridizing sequence of SEQ ID NO: 5 |
| 7 | GTTCAGCGCATATGGACGACGA | Non-T7 amp oligomer (HSV1 UL42) |
| 8 | AGACGCTGATGAAGCGCGAA | Detection probe oligomer (HSV1 UL42) |
| 9 | ACGACGACGTCCGACGGC | Non-T7 amp oligomer (HSV1 UL42) |
| 10 | GGCCGTTGAGCTAGCCA | Detection probe oligomer (HSV1 UL42) |
| 11 | aatttaatacgactcactatagggagaGGTTCCCTGGGGAACCAGCACCA | T7 amp oligomer (HSV1 UL42) |
| 12 | GGTTCCCTGGGGAACCAGCACCA | Target hybridizing sequence of SEQ ID NO: 11 |
| 13 | AATTTAATACGACTCACTATAGGGAGAAACGTGGTGGGTTTGGCGGTC | T7 amp oligomer (HSV2 UL42) |
| 14 | AACGTGGTGGGTTTGGCGGTC | Target hybridizing sequence of SEQ ID NO: 13 |
| 15 | ACGTCCAGCTGCGCCTCACGA | Non-T7 amp oligomer (HSV2 UL42) |
| 16 | TCACGAAGGTGGTGAACGC | Detection probe oligomer (HSV2 UL42) |

TABLE 17-continued

Exemplary Oligomer Sequences, Reference Sequences, and Regions

| SEQ ID NO: | Sequence 5'→3' | Description |
|---|---|---|
| 17 | GUACUGGUUGGCGCGAAACATTTAAAAAAAAAAAAAAAAAAAAAAAAAAAA | Target capture oligomer (HSV UL42) |
| 18 | GUACUGGUUGGCGCGAAACA | Target hybridizing sequence of SEQ ID NO: 17 |
| 19 | aatttaatacgactcactatagggagaTCCCTGGGGAACCAGCACCACA | T7 amp oligomer (HSV1 UL42) |
| 20 | TCCCTGGGGAACCAGCACCACA | Target hybridizing sequence of SEQ ID NO: 19 |
| 21 | uGAUGAAGCGCGAACUGACucauca | Detection probe oligomer (HSV1 UL42) |
| 22 | GAUGAAGCGCGAACUGAC | Target hybridizing sequence of SEQ ID NO: 21 |
| 23 | aatttaatacgactcactatagggagaGCAGGTGCGCGCGTTAAAC | T7 amp oligomer (HSV2 UL42) |
| 24 | GCAGGTGCGCGCGTTAAAC | Target hybridizing sequence of SEQ ID NO: 23 |
| 25 | ACGAGACCGCCAAACCCA | Non-T7 amp oligomer (HSV2 UL42) |
| 26 | CUCGGCCCCAACGGCAAGUUccgag | Detection probe oligomer (HSV2 UL42) |
| 27 | CUCGGCCCCAACGGCAAGUU | Target hybridizing sequence of SEQ ID NO: 26 |
| 28 | TCCCTGGGGAACCAGCACCA | Amp oligomer core sequence |
| 29 | GGTTCCCTGGGGAACCAGCACCACA | Amp oligomer region |
| 30 | TGGGGAACCAGC | Amp oligomer core sequence |
| 31 | GGTTCCCTGGGGAACCAGCACCACAAAGC | Amp oligomer region |
| 32 | ACGACGA | Amp oligomer core sequence |
| 33 | GTTCAGCGCATATGGACGACGACGTCCGACGGC | Amp oligomer region |
| 34 | GATGAAGCGCGAA | Probe oligomer core sequence |
| 35 | GAUGAAGCGCGAA | Probe oligomer core sequence |
| 36 | AGACGCTGATGAAGCGCGAACTGAC | Probe oligomer region |
| 37 | AGACGCUGAUGAAGCGCGAACUGAC | Probe oligomer region |
| 38 | GTTGAGCTAG | Probe oligomer core sequence |
| 39 | GGCCGTTGAGCTAGCCAGCG | Probe oligomer region |
| 40 | GGCCGTTGAGCTAGCCAGCGAGACGCTGATGAAGCGCGAACTGAC | Probe oligomer region |
| 41 | GGCCGUUGAGCUAGCCAGCGAGACGCUGAUGAAGCGCGAACUGAC | Probe oligomer region |
| 42 | TGGGTTTGGCGGTC | Amp oligomer core sequence |
| 43 | CGAACGTGGTGGGTTTGGCGGTCTCGTCC | Amp oligomer region |
| 44 | AGCTGCGCCT | Amp oligomer core sequence |
| 45 | CCGACGTCCAGCTGCGCCTCACGAAGCC | Amp oligomer region |
| 46 | GAAGGTGGTGA | Probe oligomer core sequence |
| 47 | CAGCTCACGAAGGTGGTGAACGCCGTC | Probe oligomer region |

TABLE 17-continued

Exemplary Oligomer Sequences, Reference Sequences, and Regions

| SEQ ID NO: | Sequence 5'→3' | Description |
|---|---|---|
| 48 | GTGCGCGCGTT | Amp oligomer core sequence |
| 49 | GGTGACGCAGGTGCGCGCGTTAAACACG | Amp oligomer region |
| 50 | GACCGCCAAACCCA | Amp oligomer core sequence |
| 51 | GGACGAGACCGCCAAACCCACCACGTTCG | Amp oligomer region |
| 52 | CCCCAACGGC | Probe oligomer core sequence |
| 53 | AGCUCGGCCCCAACGGCAAGUUUUC | Probe oligomer region |
| 54 | AATTTAATACGACTCACTATAGGGAGA | T7 promoter sequence |
| 69 | UGGGUGCUGGUGCUGGACGAUUUAAAAAAAAAAAAAAAAAAAAAAAAAAA | Target capture oligomer (HSV UL42) |
| 70 | UGGGUGCUGGUGCUGGACGA | Target hybridizing sequence of SEQ ID NO: 69 |
| 71 | ACCUGGGUGCUGGUGCUGGAUUUAAAAAAAAAAAAAAAAAAAAAAAAAAA | Target capture oligomer (HSV UL42) |
| 72 | ACCUGGGUGCUGGUGCUGGA | Target hybridizing sequence of SEQ ID NO: 71 |
| 73 | UGGGUGCUGGUGCUGGA | Capture oligomer core sequence |
| 74 | ACCUGGGUGCUGGUGCUGGACGA | Capture oligomer region |
| 75 | GUGCUGGUGCU | Capture oligomer core sequence |
| 76 | AUCUGGACCUGGGUGCUGGUGCUGGACGAC | Capture oligomer region |

The invention claimed is:

1. A Herpes Simplex Virus 1 (HSV-1) detection probe comprising a target-hybridizing sequence and a covalently linked non-nucleotide detectable label, wherein the target hybridizing sequence consists of the sequence of SEQ ID NO: 22.

2. The HSV-1 detection probe of claim 1, further comprising a quencher.

3. The HSV-1 detection probe of claim 2, which is a molecular torch.

4. The HSV-1 detection probe of claim 3, comprising the sequence of SEQ ID NO: 21.

5. A Herpes Simplex Virus 2 (HSV-2) detection probe comprising a target-hybridizing sequence and a covalently linked non-nucleotide detectable label, wherein the target hybridizing sequence consists of the sequence of SEQ ID NO: 27.

6. The HSV-2 detection probe of claim 5, further comprising a quencher.

7. The HSV-2 detection probe of claim 6, which is a molecular torch.

8. The HSV-2 detection probe of claim 7, comprising the sequence of SEQ ID NO: 26.

9. A combination comprising the HSV-1 detection probe of claim 1 and an HSV-2 detection probe comprising a target-hybridizing sequence and a covalently linked non-nucleotide detectable label, wherein the target hybridizing sequence of the HSV-2 detection probe consists of the sequence of SEQ ID NO: 27.

10. The combination of claim 9, wherein the HSV-1 detection probe further comprises a quencher and the HSV-2 detection probe further comprises a quencher.

11. The combination of claim 10, wherein the HSV-1 detection probe is a molecular torch and the HSV-2 detection probe is a molecular torch.

12. The combination of claim 11, wherein the HSV-1 detection probe comprises the sequence of SEQ ID NO: 21 and the HSV-2 detection probe comprises the sequence of SEQ ID NO: 26.

13. A kit comprising the combination of claim 9.

14. A kit comprising the combination of claim 12.

15. A method of determining the presence or absence of Herpes Simplex Virus 1 (HSV-1) in a sample, said method comprising contacting a sample suspected of comprising HSV-1 nucleic acid with the HSV-1 detection probe of claim 1 and determining whether the HSV-1 detection probe hybridizes to the HSV-1 nucleic acid.

16. The method of claim 15, wherein the HSV-1 nucleic acid is an HSV-1 amplification product and the HSV-1 detection probe is configured to specifically hybridize to the HSV-1 amplification product.

17. A method of determining the presence or absence of Herpes Simplex Virus 2 (HSV-2) in a sample, said method comprising contacting a sample suspected of comprising HSV-2 nucleic acid with the HSV-2 detection probe of claim 5 and determining whether the HSV-2 detection probe hybridizes to the HSV-2 nucleic acid.

18. The method of claim 17, wherein the HSV-2 nucleic acid is an HSV-2 amplification product and the HSV-2 detection probe is configured to specifically hybridize to the HSV-2 amplification product.

19. A method of determining the presence or absence of HSV-1 or HSV-2 in a sample, said method comprising contacting a sample suspected of comprising HSV-1 or HSV-2 nucleic acid with the HSV-1 detection probe of claim 1 and an HSV-2 detection probe comprising a target-hybridizing sequence and a covalently linked non-nucleotide detectable label, wherein the target hybridizing sequence of the HSV-2 detection probe consists of the sequence of SEQ ID NO: 27; and determining whether the HSV-1 detection probe hybridizes to the HSV-1 nucleic acid and whether the HSV-2 detection probe hybridizes to the HSV-2 nucleic acid.

20. The method of claim 19, wherein the HSV-1 nucleic acid is an HSV-1 amplification product and the HSV-1 detection probe is configured to specifically hybridize to the HSV-1 amplification product; and the HSV-2 nucleic acid is an HSV-2 amplification product and the HSV-2 detection probe is configured to specifically hybridize to the HSV-2 amplification product.

* * * * *